US007557115B2

(12) United States Patent
Bergnes et al.

(10) Patent No.: US 7,557,115 B2
(45) Date of Patent: Jul. 7, 2009

(54) COMPOUNDS, COMPOSITIONS, AND METHODS

(75) Inventors: Gustave Bergnes, South San Francisco, CA (US); David J. Morgans, Jr., South San Francisco, CA (US)

(73) Assignee: Cytokinetics, Inc., South San Francisco, CA (US)

( * ) Notice: Subject to any disclaimer, the term of this patent is extended or adjusted under 35 U.S.C. 154(b) by 406 days.

(21) Appl. No.: 10/529,745

(22) PCT Filed: Sep. 30, 2003

(86) PCT No.: PCT/US03/30788

§ 371 (c)(1),
(2), (4) Date: Nov. 14, 2005

(87) PCT Pub. No.: WO2004/034972

PCT Pub. Date: Apr. 29, 2004

(65) Prior Publication Data

US 2006/0264449 A1   Nov. 23, 2006

Related U.S. Application Data

(60) Provisional application No. 60/414,756, filed on Sep. 30, 2002.

(51) Int. Cl.
*A61K 31/517* (2006.01)
*C07D 239/88* (2006.01)
(52) U.S. Cl. .................... 514/266.3; 544/287
(58) Field of Classification Search ............. 514/266.3; 544/287
See application file for complete search history.

(56) References Cited

U.S. PATENT DOCUMENTS

| | | |
|---|---|---|
| 3,320,124 A | 5/1967 | Waletzky et al. |
| 3,322,756 A | 5/1967 | Ruschig et al. |
| 3,723,432 A | 3/1973 | Ott et al. |
| 3,740,442 A | 6/1973 | Ott et al. |
| 3,925,548 A | 12/1975 | Oh |
| 3,962,244 A | 6/1976 | Weyer et al. |
| 4,011,324 A | 3/1977 | Althuis |
| 4,281,127 A | 7/1981 | LeMahieu et al. |
| 4,729,996 A | 3/1988 | Wright et al. |
| 4,734,419 A | 3/1988 | Hashimoto et al. |
| 4,808,590 A | 2/1989 | Higa et al. |
| 4,857,530 A | 8/1989 | Berman et al. |
| 4,859,670 A | 8/1989 | Kampe et al. |
| 4,866,084 A | 9/1989 | Gunasekera et al. |
| 4,970,226 A | 11/1990 | Sun et al. |
| 4,981,856 A | 1/1991 | Hughes |
| 4,992,550 A | 2/1991 | Hughes |
| 5,037,829 A | 8/1991 | Freyne et al. |
| 5,081,124 A | 1/1992 | Hughes |
| 5,147,875 A | 9/1992 | Coates |
| 5,158,959 A | 10/1992 | Geiger et al. |
| 5,187,167 A | 2/1993 | Hughes |
| 5,204,354 A | 4/1993 | Chakravarty et al. |
| 5,264,439 A | 11/1993 | Greenlee et al. |
| 5,280,027 A | 1/1994 | Andrew et al. |
| 5,316,906 A | 5/1994 | Haughland et al. |
| 5,330,987 A | 7/1994 | Allen et al. |
| 5,342,944 A | 8/1994 | Mohan et al. |
| 5,401,766 A | 3/1995 | Geiger et al. |
| 5,430,148 A | 7/1995 | Webber et al. |
| 5,444,061 A | 8/1995 | Bisset et al. |
| 5,449,678 A | 9/1995 | Pines et al. |
| 5,470,878 A | 11/1995 | Michnick et al. |
| 5,492,915 A | 2/1996 | Dereu et al. |
| 5,561,133 A | 10/1996 | Bisset et al. |
| 5,574,057 A | 11/1996 | Ireland et al. |
| 5,707,992 A | 1/1998 | Webber et al. |
| 5,714,493 A | 2/1998 | Myers et al. |
| 5,747,498 A | 5/1998 | Schnur et al. |
| 5,753,664 A | 5/1998 | Aono et al. |
| 5,756,450 A | 5/1998 | Hahn et al. |
| 5,756,502 A | 5/1998 | Padia |
| 5,756,510 A | 5/1998 | Griffin et al. |
| 5,770,595 A | 6/1998 | Klein et al. |
| 5,773,476 A | 6/1998 | Chen et al. |
| 5,777,115 A | 7/1998 | Leigh et al. |
| 5,780,476 A | 7/1998 | Underiner |
| 5,783,577 A | 7/1998 | Houghten et al. |

(Continued)

FOREIGN PATENT DOCUMENTS

AU   B-12617/88   9/1988

(Continued)

OTHER PUBLICATIONS

CHEMCATS Copyright 2001 ACS, 1998:596123 CHEMCATS, Maybridge, Apr. 3, 2000, DP01489, "N2-(3-pyridylmethyl)-4-oxo-3,4-dihydroquinazoline-2-carboxamide," 190437-46-8, Chemical Library.

(Continued)

*Primary Examiner*—James O Wilson
*Assistant Examiner*—Tamthom N Truong
(74) *Attorney, Agent, or Firm*—Finnegan, Henderson, Farabow, Garrett & Dunner, LLP

(57) ABSTRACT

Compounds, compositions and methods useful for treating cellular proliferative diseases and disorders, for example, by modulating the activity of KSP, are disclosed.

28 Claims, No Drawings

U.S. PATENT DOCUMENTS

| | | | |
|---|---|---|---|
| 5,789,427 | A | 8/1998 | Chen et al. |
| 5,795,898 | A | 8/1998 | Brown et al. |
| 5,801,181 | A | 9/1998 | Michnick et al. |
| 5,801,182 | A | 9/1998 | Klein et al. |
| 5,804,584 | A | 9/1998 | Underiner et al. |
| 5,807,861 | A | 9/1998 | Klein et al. |
| 5,807,862 | A | 9/1998 | Klein et al. |
| 5,811,429 | A | 9/1998 | Connell et al. |
| 5,817,662 | A | 10/1998 | Klein et al. |
| 5,837,703 | A | 11/1998 | Kumar et al. |
| 5,852,024 | A | 12/1998 | Pines et al. |
| 5,859,018 | A | 1/1999 | Brown et al. |
| 5,869,665 | A | 2/1999 | Padia |
| 5,885,996 | A | 3/1999 | Webber et al. |
| 5,891,879 | A | 4/1999 | Nagler et al. |
| 5,892,114 | A | 4/1999 | Goldmann et al. |
| 5,922,866 | A | 7/1999 | Miyata et al. |
| 5,929,081 | A | 7/1999 | Brown et al. |
| 5,939,421 | A | 8/1999 | Palanki et al. |
| 5,948,775 | A | 9/1999 | Koko et al. |
| 5,948,784 | A | 9/1999 | Fujiwara et al. |
| 6,008,010 | A | 12/1999 | Greenberger et al. |
| 6,136,812 | A | 10/2000 | Chenard et al. |
| 6,156,758 | A | 12/2000 | Kung et al. |
| 6,207,403 | B1 | 3/2001 | Goldstein et al. |
| 6,214,879 | B1 | 4/2001 | Abraham et al. |
| 6,245,768 | B1 | 6/2001 | He et al. |
| 6,518,277 | B1 | 2/2003 | Sadhu et al. |
| 6,545,004 | B1 | 4/2003 | Finer et al. |
| 6,545,005 | B1 | 4/2003 | Baxter et al. |
| 6,559,160 | B1 | 5/2003 | Schall et al. |
| 6,562,831 | B1 | 5/2003 | Finer et al. |
| 6,596,723 | B1 | 7/2003 | Watkins et al. |
| 6,613,798 | B1 | 9/2003 | Porter et al. |
| 6,627,755 | B1 | 9/2003 | Chenard et al. |
| 6,630,479 | B1 | 10/2003 | Finer et al. |
| 6,753,428 | B2 | 6/2004 | Bergnes et al. |
| 6,794,379 | B2 | 9/2004 | Medina et al. |
| 6,831,085 | B1 | 12/2004 | Bergnes et al. |
| 2001/0046997 | A1 | 11/2001 | Abraham et al. |
| 2002/0032207 | A1 | 3/2002 | Thompson et al. |
| 2002/0055519 | A1 | 5/2002 | Thompson et al. |
| 2002/0165221 | A1 | 11/2002 | Baxter et al. |
| 2002/0169159 | A1 | 11/2002 | Medina et al. |
| 2002/0198326 | A1 | 12/2002 | Aoyama et al. |
| 2003/0018038 | A1 | 1/2003 | Thompson et al. |
| 2003/0055054 | A1 | 3/2003 | Medina et al. |
| 2003/0091946 | A1 | 5/2003 | Uchira et al. |
| 2003/0096813 | A1 | 5/2003 | Cao et al. |
| 2003/0119834 | A1 | 6/2003 | Bamdad |
| 2003/0119854 | A1 | 6/2003 | Schall et al. |
| 2003/0130293 | A1 | 7/2003 | Bamdad |
| 2003/0139398 | A1 | 7/2003 | Hoekstra et al. |
| 2003/0139457 | A1 | 7/2003 | Baxter et al. |
| 2003/0144350 | A1 | 7/2003 | Stevenson et al. |
| 2003/0158188 | A1 | 8/2003 | Lee et al. |
| 2003/0158198 | A1 | 8/2003 | Lee et al. |
| 2003/0166933 | A1 | 9/2003 | Bergnes et al. |
| 2003/0171387 | A1 | 9/2003 | Sun et al. |
| 2003/0195211 | A1 | 10/2003 | Sadhu et al. |
| 2003/0220338 | A1 | 11/2003 | Watkins et al. |
| 2003/0220356 | A1 | 11/2003 | Ibrahim et al. |
| 2004/0023996 | A1 | 2/2004 | Finer et al. |
| 2004/0048853 | A1 | 3/2004 | Bergnes |
| 2004/0067969 | A1 | 4/2004 | Bergnes et al. |
| 2004/0077662 | A1 | 4/2004 | Zhou et al. |
| 2004/0077667 | A1 | 4/2004 | Matsuoka et al. |
| 2004/0077668 | A1 | 4/2004 | Feng et al. |
| 2004/0082567 | A1 | 4/2004 | McDonald et al. |
| 2004/0092561 | A1 | 5/2004 | Ruckle et al. |
| 2004/0116438 | A1 | 6/2004 | Lu et al. |
| 2004/0142949 | A1 | 7/2004 | Bergnes et al. |
| 2004/0192913 | A1 | 9/2004 | Bergnes et al. |
| 2004/0198724 | A1 | 10/2004 | McNaughton-Smith et al. |
| 2004/0242596 | A1 | 12/2004 | Kim et al. |
| 2004/0259826 | A1 | 12/2004 | Fraley et al. |
| 2005/0059823 | A1 | 3/2005 | McNaughton-Smith et al. |
| 2005/0152940 | A1 | 7/2005 | Hezi-Yamit et al. |
| 2005/0209254 | A1 | 9/2005 | Wang et al. |

FOREIGN PATENT DOCUMENTS

| | | |
|---|---|---|
| EP | 0 056 637 A1 | 7/1982 |
| EP | 0 286 813 A2 | 2/1988 |
| EP | 0 341 990 A3 | 11/1989 |
| EP | 0 341 990 B1 | 11/1989 |
| EP | 0 360 417 A2 | 3/1990 |
| EP | 0 360 417 A3 | 3/1990 |
| EP | 0 373 891 A2 | 6/1990 |
| EP | 0 431 945 A2 | 6/1991 |
| EP | 0 481 614 A1 | 4/1992 |
| EP | 0 509 643 A1 | 10/1992 |
| EP | 0 512 676 A1 | 11/1992 |
| EP | 0 534 706 A1 | 3/1993 |
| EP | 0 537 937 A2 | 4/1993 |
| EP | 0 884 310 A1 | 12/1998 |
| EP | 0 884 316 A1 | 12/1998 |
| EP | 0 884 319 A2 | 12/1998 |
| EP | 0 884 319 A3 | 12/1998 |
| EP | 0 900 568 A2 | 3/1999 |
| EP | 0 903 344 A1 | 3/1999 |
| EP | 1 072 952 A1 | 1/2000 |
| EP | 1 174 430 A1 | 1/2002 |
| GB | 2271111 A | 4/1994 |
| HU | 184797 | 10/1984 |
| JP | 62-135473 | 6/1987 |
| JP | 06049070 A2 | 2/1994 |
| JP | 06-148835 | 5/1994 |
| JP | 10/259176 | 9/1998 |
| WO | WO 91/12001 A1 | 8/1991 |
| WO | WO 93/11115 A2 | 6/1993 |
| WO | WO 93/19051 A1 | 9/1993 |
| WO | WO 93/20055 A1 | 10/1993 |
| WO | WO 93/23404 A1 | 11/1993 |
| WO | WO 94/21259 A1 | 9/1994 |
| WO | WO 95/16682 A1 | 6/1995 |
| WO | WO 95/19169 A2 | 7/1995 |
| WO | WO 95/24379 A1 | 9/1995 |
| WO | WO 96/06616 A1 | 3/1996 |
| WO | WO 96/19224 A1 | 6/1996 |
| WO | WO 96/28430 A1 | 9/1996 |
| WO | WO 96/28444 A1 | 9/1996 |
| WO | WO 96/39403 A1 | 12/1996 |
| WO | WO 97/10221 A1 | 3/1997 |
| WO | WO 97/43276 A1 | 11/1997 |
| WO | WO 98/26664 A1 | 6/1998 |
| WO | WO 98/29410 A1 | 7/1998 |
| WO | WO 98/34613 A1 | 8/1998 |
| WO | WO 98/58947 A1 | 12/1998 |
| WO | WO 99/08501 A2 | 2/1999 |
| WO | WO 99/20298 A1 | 4/1999 |
| WO | WO 00/00491 A1 | 1/2000 |
| WO | WO 00/07017 A2 | 2/2000 |
| WO | WO 01/74344 A2 | 10/2000 |
| WO | WO 00/69827 A1 | 11/2000 |
| WO | WO 01/16114 A2 | 3/2001 |
| WO | WO 01/19800 A2 | 3/2001 |
| WO | WO 01/23364 A1 | 4/2001 |
| WO | WO 01/23365 A1 | 4/2001 |
| WO | WO 01/25235 A1 | 4/2001 |
| WO | WO 01/30768 A1 | 5/2001 |
| WO | WO 01/32171 A1 | 5/2001 |
| WO | WO 01/32634 A1 | 5/2001 |
| WO | WO 01/42216 A2 | 6/2001 |

| | | | |
|---|---|---|---|
| WO | WO 01/66519 A2 | 9/2001 |
| WO | WO 01/70737 A2 | 9/2001 |
| WO | WO 01/81346 A2 | 11/2001 |
| WO | WO 01/95884 A2 | 12/2001 |
| WO | WO 01/98278 A1 | 12/2001 |
| WO | WO 02/04444 A2 | 1/2002 |
| WO | WO 02/08224 A1 | 1/2002 |
| WO | WO 02/09713 A2 | 2/2002 |
| WO | WO 02/09713 A3 | 2/2002 |
| WO | WO 02/14319 A2 | 2/2002 |
| WO | WO 02/30462 A2 | 4/2002 |
| WO | WO 02/083143 A1 | 10/2002 |
| WO | WO 02/094790 A1 | 11/2002 |
| WO | WO 03/020279 A2 | 3/2003 |
| WO | WO 03/020280 A2 | 3/2003 |
| WO | WO 03/027234 A2 | 4/2003 |
| WO | WO 03/035076 A1 | 5/2003 |
| WO | WO 03/035077 A1 | 5/2003 |
| WO | WO 03/039460 A2 | 5/2003 |
| WO | WO 03/043961 A2 | 5/2003 |
| WO | WO 03/043995 A1 | 5/2003 |
| WO | WO 03/049527 A2 | 6/2003 |
| WO | WO 03/049678 A2 | 6/2003 |
| WO | WO 03/049679 A2 | 6/2003 |
| WO | WO 03/050064 A2 | 6/2003 |
| WO | WO 03/050122 A2 | 6/2003 |
| WO | WO 03/063800 A2 | 8/2003 |
| WO | WO 03/070701 A2 | 8/2003 |
| WO | WO 03/070701 A3 | 8/2003 |
| WO | WO 03/076418 A1 | 9/2003 |
| WO | WO 03/079973 A2 | 10/2003 |
| WO | WO 03/084544 A2 | 10/2003 |
| WO | WO 03/094839 A2 | 11/2003 |
| WO | WO 03/097053 A1 | 11/2003 |
| WO | WO 03/099211 A2 | 12/2003 |
| WO | WO 03/103575 A2 | 12/2003 |
| WO | WO 03/105855 A1 | 12/2003 |
| WO | WO 03/106417 A1 | 12/2003 |
| WO | WO 03/106426 A1 | 12/2003 |
| WO | WO 03/106435 A1 | 12/2003 |
| WO | WO 2004/004652 A2 | 1/2004 |
| WO | WO 2004/006916 A1 | 1/2004 |
| WO | WO 2004/009036 A2 | 1/2004 |
| WO | WO 2004/018058 A2 | 3/2004 |
| WO | WO 2004/020599 A2 | 3/2004 |
| WO | WO 2004/022554 A2 | 3/2004 |
| WO | WO 2004/034972 A2 | 4/2004 |
| WO | WO 2004/039774 A2 | 5/2004 |
| WO | WO 2004/064741 A2 | 8/2004 |
| WO | WO 2004/078758 | 9/2004 |

OTHER PUBLICATIONS

Q. Kozhevnikov et al. 4-Quinazolinones. II. 2-(Aminomethyl)-3-aryl-4-quinazolinones. (Russian) Tr Perm Sel-Khoz Inst. 79: 66-72 (1971). Chem Abstracts 78: 390 (1973).

Gupta, C.M. et al. "Drugs acting on the central nervous system. Synthesis of substituted quinazolones and quinazolines and triazepino- and triazocinoquinazolones," *J. Med. Chem.* 11: 392-395 (1968).

Saari, W.S. et al. "Synthesis and evaluation of 2-pyridinone derivatives as HIV-1-specific reverse transcriptase inhibitors. 2. Analogues of 3-aminopyridin-2(1H)-one," *J. Med. Chem.* 35: 3792-3802 (1992).

Farghaly, A.M. et al. "Non-steroidal anti-inflammatory agents. III: Synthesis of pyrazole derivatives of 4(3H)-quinazolinones," *Alexandria J. Pharm. Sci.* 4(1): 52-56 (1990).

Dymek, W. et al. "2-Chloromethyl-6-methylquinazolone-4 and its transformations," *Diss. Pharm. Et Pharmacol.* 20(1): 29-34 (1968).

Pattanaik, J.M. et al. "Synthesis and fungicidal activity of 3-aryl-2-(4'-aryl thiazol-2'-ylaminomethyl) quinazol-4(3H)-ones," *Indian J. Chem.* 37B: 1304-1306 (1998).

Gupta, D.P., e t al. "Thiazolidinones, azetidinones and formazans of quinazolinones," *Indian J. Chem.* 26B: 1197-1199 (1987).

Parasharya, P.M. et al. "4(3H)-Quinazolones. Part 1: 2-Alkyl/arylaminomethyl-3-p-hydroxy/methoxyphenyl-4(3H)-quinazolones," J. Inst. Chemists (India) 64: 184-185 (1992).

Parasharya, P.M. et al. "4-(3H)-Quinazolones: 2-N-aryl/alkyl-amino-methyl/ethyl-3-p-hydroxyphenyl/p-anisyl/p-arylaminoacyloxyphenyl/p-N-arylcarbamoylmethoxyphenyl-4-(3H)-quinazolones," *J. Inst. Chemists* (India) 64: 238-241 (1992).

Matthews, N. et al. "Structure-activity relationships of phenothiazines in inhibiting lymphocyte motility as determined by a novel flow cytometric assay," *Biochem. Pharmcol.* 50(7): 1053-1061 (1995).

List of Purchased Compounds 10/00.

Debnath, A.K. "Structure-Based Identification of Small Molecule Antiviral Compounds Targeted to the gp41 Core Structure of the Human Immunodeficiency Virus Type 1," *J. Med. Chem.* 42 (17): 3203-3209 (1999).

Mayer et al. "Solid phase synthesis of quinazolinones" *Tet. Lett.* 38(49):8445-8448 (1997).

Prashad et al. "Reaction of benzoyleneurea and isatoic anhydride with the Vilsmeier reagent" *Tet. Lett.* 38(8):1313-1316 (1997).

Villalgordo et al. "Solid-phase synthesis of 3H-quinazolin-4-ones based on an aza Wittig-mediated annulation strategy" *Synlett* 1405-1407 (1998).

Wuckelt et al. "Efficient synthesis of quinazolin-4-ones and axially chiral 2,2'-bis-quinazolin-4-ones by reaction of anthranilic acid derived nucleophiles with oxalic acid-bis(imidoyl)chlorides." *Synlett* 7:1100-1102 (1999).

Wang et al. "Total synthesis of the quinazolinone alkaloids (-)-Fumiquinazoline G and (-)-Fiscalin B" *J. Org. Chem.* 63:2432-2433 (1998).

Padia et al. "Novel nonpeptide CCK-B antagonists: Design and development of quinazolinone derivatives as potent, selective, and orally active CCK-B antagonists" *J. Med. Chem.* 41:1042-1049 (1998).

Singh et al. "4-Quinazolones-II Synthesis of some imidazo [1,5-a] quinazolones" *J. Indian Chem. Soc.* 46(1):21-25 (1969).

Badawy et al. "Chemistry of Quinazolines: Reinvestigation of the Action of Hydrazine on Thioxo Derivatives" *J. Heterocyclic Chem.* 22: 1535-1536 (1985).

Yu et al. "Synthesis and x-ray crystallographic analysis of quinazolinone cholecystokinin/gastrin receptor ligands" *J. Med. Chem.* 35:2534-2542 (1992).

Zaher et al. "Reactions of 2-p-anisyl-3(4H), 1-benzoxazin-4-one with ammonia, primary amines, hydrazine, phenylhydrazine & Grignard reagents" *Indian J. Chem.* 12:1212-1215 (1974).

Kulkarni et al. "Possible antifertility agents. Part-I. Synthesis of 2-(N,N-substituted-aminomethyl)-3-(2-pyridyl)-4(3H)-oxo-3, 1-quinazolines" *J. Indian Chem.* LXI:720-721 (1984).

Majo et al. "Dimerization of substituted 2-aminobenzoic acids under Vilsmeier conditions: A novel route to the synthesis of 4-(3H)-quinazolinones" *Tet. Lett.* 37(28):5015-5018 (1996).

Rathman et al. "Functionalization of 2-methyl-3-o-tolyl-4(3H)-quinazolinone and related compounds through carbanion reactions at the 2-methyl group" *J. Org. Chem.* 45:2169-2176 (1980).

Padia et al. "Design and synthesis of novel nonpeptide CCK-B receptor antagonists" *Bioorg. Med. Chem. Lett.* 7(7):805-810 (1997).

Zentmyer et al. "The so-called acylanthranils (3,1,4-benzoxazones). I. Preparation; reactions with water, ammonia, and aniline; structure" *J. Organic Chemistry*, 14: 967-981 (1949).

Panday, V.K. "Possible Antiparkinsonian Compounds Part XI: Synthesis of 2-aryl/alkyl-3-[β-(3'-4'-dihydroxyphenyl) ethyl]-quinazolin (3H)-4-one and 2-aryl/alkyl-3-[(7'-(phenothiazinyl)-ethyl]-quinazolin/(3H)-4-one" *Acta Ciencia Indica* 4(3):230-235 (1978).

Tiwari et al. Chemical Abstracts, vol. 96, Abstract No. 142790p (1982).

Fadda et al. "Reactions of a heterocyclic β-enaminoester: Synthesis of pyranopyrimidines and pyrano[3', 2', : 5,6]pyrimidino[2, 3-c][1,4]benzoxazine ring system," *Indian J. Chemistry* 29B: 1020-1024 (1990).

Wagner "Synthesis and Biological Evaluation of Some Derivatives of Pyrido[3, 2-d]pyrimidine" *Acta Poloniae Pharmaceutica—Drug Research* 51(4-5): 359-363 (1994).

El-Sharief et al. "Oxidation of 3-aminoquinazolinones with lead tetraacetate. A novel synthesis of naphtho-fused azirino-pyrazolo and 1,4,5-oxadiazepino-quinazolinones" *J. Chem Research (S)*: 205-208 (2002).

Chenard et al. "Quinazolin-4-one α-Amino-3-hydroxy-5-methyl-4-isoxazolepropionic Acid (AMPA) Receptor Antagonists: Structure-Activity Relationship of the C-2 Side Chain Tether" *J. Med. Chem* 44:1710-1717 (2001).

Garg et al. "Synthesis and anti-implantation activity of α-(2-aryl-3-ethyl-4-oxo (3H) quinazolinyl)-α-(substituted styrl)-cyclohexanone thiosemicarbazones" *Biol. Mem.* 14(2): 180-186 (1988).

Singh et al. "Synthesis and pharmacological screening of some 2-aryl-3-(phenyl-aryl-hydrazonyl)-quinazolin (3H) 4-ones" *Indian Drugs* 28(2):70-74 (1990).

Ahmad et al. "Monoamine oxidase Inhibitory Activity of 4 (3H)-Quinazolinones of Dopamine" *Indian J. of Pharm. Sci.* 126-127 (1979).

Tiwari et al. "Possible Antifertility Compounds Part III: Synthesis of 2-Hippuryl-3-Aryl-Quinazolinones" *J. Chem. Soc. Pak.* 3(4):215-217 (1981).

Pandey, V.K. "Antiparkinsonism and CNS Activities of 2-aryl alkyl-3-{β-(3'-4'- dihydroxyphenyl) Ethyl}-quinazolin (3H) 4-ones" *Biol. Mem.* 11(2):213-215 (1985).

Monika et al. "Uj kinazolonszarmazekok szintezise es ciklizalasa [1,4]oxazepino- es [1,4]diazepino [3,4-b]kinazolonkka" *Magyar Kemiai Folyoirat*102(8):343-355 (1996) translated abstract.

Reddy et al. "A New Synthesis of 2-aryl-2H-Pyrazino[2,1-β]Quinazolin-3,6(1H,4H)-Diones" *Synthetic Communications* 21(2):173-181 (1991).

Monika et al. "Potencialis CCK-antagonista kinazolon-szarmazekok szintezse" *Acta Pharm. Hungarica* 65: 133-136 (1995) translated abstract.

Pandey et al. "Quinazolyl-thiazoles as CNS acting agents" *Acta Pharm.* 46:51-59 (1996).

Reddy et al. "4-Heteryl-β-lactams: A facile synthesis of 1-aryl-4-[isopropylideneamino/methyl-4(3H)-oxoquinazolin-2-yl] azetidin-2-ones" *Indian J. of Chem.* 38B:40-44 (1999).

Reddy et al. "Bisazaheterocycles: Part VII—Synthesis of novel bisquinazolinonyl β-lactams" *Ind. J. of Chem.* 41B: 1946-1949 (2002).

Krisztina et al. "Az AGP-alapu folyadek-kromatografias allofazis alkalmazasa kinazolon szarmazekok enantiomerjeinek elvalasztasaban" *Acta Pharma. Hungarica* 73:5-12 (2003) translated abstract.

Reddy et al. "Synthesis of 2-quinazolinonyl imidazolidinones" *Ind. J. of Chem.* 42B:393-396 (2003).

Gyimesi-Forras et al. "Optical Resolution of a Series of Potential Cholecystokinin Antagonist 4(3H)-Quinazolone Derivatives by Chiral Liquid Chromatography on α₁-Acid Glycoprotein Stationary Phase" *J. of Chromat. Sci.* 38:430-434 (2000).

Jiang et al. "A Salt Bridge between an N-terminal Coiled Coil of gp41 and an Antiviral Agent Targeted to the gp41 Core Is Important for Anti-HIV-1 Activity" *Biochem. and Biophys. Res. Communications* 270:153-157 (2000).

Hughes et al. "Quinazoline Antifolate Thymidylate Synthase Inhibitors: Alkyl, Substituted Alkyl, and Aryl Substituents in the C2 Position" *J. Med. Chem.* 33:3060-3067 (1990).

Hassanein et al. "Sythesis of 2-substituted-10H-[1,2,4] triazino [6,1-b] quinazoline-10-ones and 8,13,14,16 tetrahydronaphtho [2',3',:3,4] [1,2,5] triazepino [7, 1-b] quinazoline-8, 13,16-triones with biological interest" *Al-Azhar Bull. Sci.* 8(2):417-434 (1997).

Szabo et al. "Nitrogen Bridgehead Compounds: Part 88 [1], Synthesis of 3H, 7H-[1,4]Diazepino[3,4-b]quinazoline-3,7-diones" *J. Heterocyclic Chem.* 34(21):21-25 (1997).

Kokosi et al. "Nitrogen Bridgehead Compounds Part 90. An Efficient Versatile Synthesis of 1-Methyl-2-substituted 1,2,3,4-Tetrahydro-6H-Pyrazino[2,1-b]Quinazoline-3,6-Diones" *Heterocycles* 48(9):1851-1866 (1998).

El-Maghraby et al. "Synthesis of Glycylaminothiazoles" *Ind. J. Chem.* 12:1058-1059 (1974).

Hassan et al. "Synthesis and antimicrobial activity of some new N-aminoacyl derivatives of 2-amino-4-phenylthiazole" *Acta Pharm.* 47:159-166 (1997).

West, "Solid State Chemistry and it's Applications," Wiley, New York, 1988, pp. 358 & 365.

Office Action mailed May 7, 2001 for U.S. Appl. No. 09/699,047, filed Oct. 24, 2000.

Office Action mailed Apr. 24, 2002, for U.S. Appl. No. 09/699,047, filed Oct. 24, 2000.

Office Action mailed Feb. 6, 2002, for U.S. Appl. No. 09/724,644, filed Nov. 28, 2000.

Office Action mailed Oct. 21, 2002, for U.S. Appl. No. 09/724,644, filed Nov. 28, 2000.

Office Action mailed Feb. 6, 2002, for U.S. Appl. No. 09/724,712, filed Nov. 28, 2000.

Office Action mailed Apr. 9, 2002, for U.S. Appl. No. 09/724,713, filed Nov. 28, 2000.

Office Action mailed Oct. 21, 2002, for U.S. Appl. No. 09/724,713, filed Nov. 28, 2000.

Office Action mailed Mar. 22, 2002, for U.S. Appl. No. 09/724,897, filed Nov. 28, 2000.

Office Action mailed Dec. 17, 2002, for U.S. Appl. No. 09/724,897, filed Nov. 28, 2000.

Office Action mailed Jul. 11, 2003, for U.S. Appl. No. 09/724,897, filed Nov. 28, 2000.

Office Action mailed May 12, 2004, for U.S. Appl. No. 09/724,897, filed Nov. 28, 2000.

Office Action mailed Jul. 26, 2002, for U.S. Appl. No. 09/724,941, filed Nov. 28, 2000.

Office Action mailed Jan. 13, 2003, for U.S. Appl. No. 09/724,941, filed Nov. 28, 2000.

Office Action mailed Jan. 7, 2004, for U.S. Appl. No. 09/724,941, filed Nov. 28, 2000.

Office Action mailed Jul. 3, 2002, for U.S. Appl. No. 09/724,778, filed Nov. 28, 2000.

Office Action mailed Dec. 27, 2002, for U.S. Appl. No. 09/724,778, filed Nov. 28, 2000.

Office Action mailed Aug. 8, 2003, for U.S. Appl. No. 09/724,778, filed Nov. 28, 2000.

Office Action mailed Dec. 29, 2003, for U.S. Appl. No. 09/724,778, filed Nov. 28, 2000.

Office Action mailed Mar. 30, 2004, for U.S. Appl. No. 09/724,778, filed Nov. 28, 2000.

Office Action mailed Jun. 25, 2004, for U.S. Appl. No. 09/724,778, filed Nov. 28, 2000.

International Search Report mailed Feb. 22, 2001, for PCT Application No. PCT/US00/29585, filed Oct. 26, 2000.

Written Opinion mailed Sep. 21, 2001, for PCT Application No. PCT/US00/29585, filed Oct. 26, 2000.

International Preliminary Examination Report mailed Jan. 17, 2002, for PCT Application No. PCT/US00/29585, filed Oct. 26, 2000.

Office Action mailed Aug. 8, 2003, for U.S. Appl. No. 10/300,967, filed Nov. 20, 2002.

International Search Report mailed Feb. 7, 2003, for PCT Application No. PCT/US02/37410, filed Nov. 20, 2002.

Written Opinion mailed Sep. 9, 2003, for PCT Application No. PCT/US02/37410, filed Nov. 20, 2002.

International Preliminary Examination Report mailed Aug. 11, 2004, for PCT Application No. PCT/US02/37410, filed Nov. 20, 2002.

International Search Report mailed Oct. 31, 2002, for PCT Application No. PCT/US01/13901, filed Apr. 27, 2001.

International Search Report mailed Oct. 17, 2003, for PCT Application No. PCT/US03/18778, filed Jun. 12, 2003.

Office Action mailed Oct. 18, 2004, for U.S. Appl. No. 10/462,002, filed Jun. 12, 2003.

Written Opinion mailed Mar. 2, 2004, for PCT Application No. PCT/US03/18778, filed Jun. 12, 2003.

International Preliminary Examination Report mailed Sep. 8, 2004, for PCT Application No. PCT/US03/18778, filed June 12, 2003.

International Search Report and Written Opinion mailed Dec. 6, 2004, for PCT Application No. PCT/US04/01279, filed Jan. 20, 2004.

International Search Report mailed Aug. 29, 2003, for PCT Application No. PCT/US03/14787, filed May 9, 2003.
Written Opinion mailed Jun. 10, 2004, for PCT Application No. PCT/US03/14787, filed May 9, 2003.
International Preliminary Examination Report mailed Nov. 16, 2004, for PCT Application No. PCT/US03/14787, filed May 9, 2003.
International Search Report mailed Jul. 16, 2004, for PCT Application No. PCT/US03/13627, filed May 2, 2003.
Office Action mailed Nov. 2, 2004, for U.S. Appl. No. 10/366,858, filed Feb. 14, 2003.
International Search Report mailed Aug. 12, 2003, for PCT Application No. PCT/US03/04713, filed Feb. 14, 2003.
Written Opinion mailed Jun. 24, 2004, for PCT Application No. PCT/US03/04713, filed Feb. 14, 2003.
International Preliminary Examination Report mailed Dec. 8, 2004, for PCT Application No. PCT/US03/04713, filed Feb. 14, 2003.
International Search Report mailed Jul. 9, 2004, for PCT Application No. PCT/US03/23319, filed Jul. 23, 2003.
International Preliminary Examination Report mailed Sep. 30, 2004, for PCT Application No. PCT/US03/23319, filed Jul. 23, 2003.
International Search Report mailed May 20, 2004, for PCT Application No. PCT/US03/26093, filed Aug. 20, 2003.
International Preliminary Examination Report mailed Aug. 5, 2004, for PCT Application No. PCT/US03/26093, filed Aug. 20, 2003.
Office Action mailed Jan. 4, 2005, for U.S. Appl. No. 10/444,283, filed May 22, 2003.
International Search Report mailed Dec. 18, 2003, for PCT Application No. PCT/US03/16500, filed May 22, 2003.
International Preliminary Examination Report mailed Jun. 23, 2004, for PCT Appl. No. PCT/US03/16500, filed May 22, 2003.
Bergnes et al., "Compounds, Compositions, and Methods," U.S. Appl. No. 10/980,627, filed Nov. 2, 2004.
Bergnes, "Compounds, Compositions, and Methods," U.S. Appl. No. 10/982,195, filed Nov. 5, 2004.
Bergnes, "Compounds, Compositions, and Methods," U.S. Appl. No. 11/005,629, filed Dec. 7, 2004.
Written Opinion mailed Sep. 24, 2004, for PCT Application No. PCT/US02/41309, filed Dec. 20, 2002.
International Search Report mailed Oct. 12, 2004, for PCT Application No. PCT/US03/30788, filed Sep. 30, 2003.
Office Action mailed Feb. 7, 2005, for U.S. Appl. No. 10/435,069, filed May 8, 2005.
International Preliminary Examination Report mailed Jan. 28, 2005, for PCT Application No. PCT/US03/30788, filed Sep. 30, 2003.
Office Action mailed Apr. 27, 2005, for U.S. Appl. No. 10/429,195, filed May 2, 2003.
International Preliminary Examination Report mailed May 9, 2005, for PCT Application No. PCT/US03/13627, filed May 2, 2003.
International Search Report and Written Opinion mailed Apr. 28, 2005, for PCT Application No. PCT/US04/36253, filed Nov. 2, 2004.
International Search Report and Written Opinion mailed Jun. 14, 2005, for PCT Application No. PCT/US04/36853, filed Nov. 5, 2004.
Sauter et al., Caplus Abstract No. 87:84931 (1977).
Uchida et al., Caplus Abstract No. 81:152142 (1974).
Yamada et al., Caplus Abstract No. 134:252363 (2001).
Matsuoka et al., Caplus Abstract No. 133:150920 (2000).
Nugent et al., Caplus Abstract No. 123:143921 (1995).
De Melo et al., Caplus Abstract No. 117:143023 (1992).
Irikura et al., Caplus Abstract No. 105:42834 (1986).
Kyorin Pharmaceutical Co., Ltd., Caplus Abstract No. 103:87901 (1985).
Shuto et al., Caplus Abstract No. 90:72134 (1979).
Katagiri et al., Caplus Abstract No. 100:51536 (1984).
Jiang et al., "Synthesis and Biological Evaluation of 2-Styrylquinazolin-4(3H)-ones, a New Class of Antimitotic Anticancer Agents Which Inhibit Tubulin Polymerization," *J. Med. Chem.*, 33: 1721-1728 (1990).
Smith et al., "Effects of Gastrin, Proglumide, and Somatostatin on Growth of Human Colon Cancer," *Gastroenterology*, 95: 1541-1548 (1988).
"Signal Transduction," from the *Dictionary of Biology*, Penguin Books, Ninth Edition reprinted with minor revisions, pp. 574-575 (1995).

"Hyper-," from *The British Medical Dictionary*, Caxton, p. 706 (circa 1961).
"Inhibit," from *The British Medical Dictionary*, Caxton, p. 747 (circa 1961).
Ghosh, "Quinazolines. Part I.," *J. Indian Chemical Society*, XIV: 411-413 (1937).
Ager et al. "Synthesis and Central Nervous System Activity of Quinazolones Related to 2-Methyl-3(o-tolyl)-4(3H) quinazolone (Methaqualone)," *J. Med. Chem.* 20(3): 379-386 (1977).
Coleman et al. "Inhibitors of the mitotic kinesin spindle protein" *Expert Opin. Ther. Patents* 14(12): 1659-1667 (2004).
Rao et al. "Synthesis and Biological Activities of Certain Derivatives of 3-Aryl-4(3H)-quinazolinones, Part-II," *J. Indian Chem. Soc.* LXII: 234-237 (1985).
Bocskei, Z. et al.. "Two Antithrombotic Quinazolone Derivatives." *Acta Crystallogr., Sect. C: Cryst. Struct. Commun.* C51(4): 723-726 (1995).
Szabo, M. et al. "Synthesis of Potential CCK Antagonist Quinazolone Derivatives," Chemical Abstracts, vol. 124, No. 13, Abstract No. 176002v (1996).
Ager et al. "Synthesis and Central Nervous System Activity of Quinazolones Related to 2-Methyl-3-(o-tolyl)-4(3H) quinazolone (Methaqualone)," *J. Med. Chem.* 20(3): 379-386 (1977).
Tiwari et al. "Synthesis and CNS Activity of 2-Aryl-3(3'-,4'-Dihydroxyphenylethyl) 6-8-substituted-4 (3H)Quinazolinones," *Indian J. Pharm. Sci.* pp. 40-43 (1978).
Rao et al. "Synthesis and Biological Activities of Certain Derivatives of 3-Aryl-4(3H)-quinazolinones, Part-II," *J. Indian Chem. Soc.* LXII: 234-237 (1985).
Commercially available from ComGenex, Sep. 16, 1999.
Registry File Compounds from Published References, Maybridge Catalog, Apr. 3, 2000.
Singh et al. Chemical Abstracts, vol. 92, Abstract No. 58712 (1980).
Spirkova et al., Chemical Abstracts, vol. 132, Abstract No. 35672 (1999).
Pandey et al. Chemical Abstracts, vol. 124, Abstract No. 331723 (1996).
Parasharya et al. Chemical Abstracts, vol. 121, Abstract No. 108675 (1994).
Saari et al. Chemical Abstracts, vol. 117, Abstract No. 191731 (1992).
Farghaly et al. Chemical Abstracts, vol. 114, Abstract No. 122242 (1991).
El-Nasser Ossman et al. Chemical Abstracts, vol. 106, Abstract No. 207516 (1987).
Rao et al. Chemical Abstracts, vol. 105, Abstract No. 97416 (1986).
Gupta et al. Chemical Abstracts, vol. 69, Abstract No. 42637 (1968).
Kumar et al. Chemical Abstracts, vol. 102, Abstract No. 142800 (1985).
Chaurasia et al. Chemical Abstracts, vol. 96, Abstract No. 6681 (1982).
Tani et al. Chemical Abstracts, vol. 93, Abstract No. 26374 (1980).
Ager et al. Chemical Abstracts, vol. 86, Abstract No. 83505 (1977).
Kozhevnikov et al. Chemical Abstracts, vol. 78, Abstract No. 16128U (1971).
Bergman et al. "Synthesis of Chrysogine, a Metabolite of *Penicillium chrysogenum* and some related 2-substituted 4-(3H)-Quinazolinones," *Tetrahedron* 46: 1295-1310 (1990).
Hart et al. "Synthesis of (-)-Alantrypinone," *Tet. Lett.* 40:5429-5432 (1999).
Hart et al. "Synthesis of *ent*-Alantrypinone" *J. Am. Chem. Soc.* 123:5892-5899. (2001).
Hegrand et al., Caplus Abstract No. 80:95873 (1974).
Witkop et al., Caplus Abstract No. 75:77191 (1971).
Office Action mailed Jun. 24, 2005, for U.S. Appl. No. 10/773,602, filed Feb. 6, 2004.
Office Action mailed Jul. 6, 2005, for U.S. Appl. No. 10/982,195, filed Nov. 5, 2004.
Gavezzotti "Are Crystal Structures Predictable" *Acc. Chem. Res.* 27:309-314 (1994).
Wolff (ed.) *Burger's Medicinal Chemistry and Drug Discovery, 5th Edition vol. 1: Principles and Practice*, John Wiley & Sons, New York, pp. 975-977 (1995).

Banker et al. (eds.) *Modern Pharmaceuticals Third Edition, Revised and Expanded*, Marcel Dekker, Inc., New York, pp. 451 & 596 (1996).

Coleman et al. "Inhibitors of the mitotic kinesin spindle protein" *Expert Opin. Ther. Patents* 14(12):1659-1667 (2004).

Li et al. "Discovery and development of antimitotic agents that inhibit tubulin polymerisation for the treatment of cancer" *Expert Opin. Ther. Patents* 12(11): 1663-1702 (2002).

Malik et al., "Compositions, Devices and Methods for Treating Cardiovascular Disease," U.S. Appl. No. 11/147,406, filed Jun. 7, 2005.

International Search Report and Written Opinion mailed Oct. 21, 2005, for PCT Application No. PCT/US05/19791, filed Jun. 7, 2005.

Franco et al., "Functional association of retinoic acid and *hedgehog* signaling in *Xenopus* primary neurogenesis," *Development*, 126: 4257-4265 (1999).

Gaffield et al., "A Looking Glass Perspective: Thalidomide and Cyclopamine," *Cellular and Molecular Biology*, 45(5): 579-588 (1999).

Ghorab, "Synthesis of Some New Thiadiazole, Selena, Triazine, Thiazole and Cyanopyridine Derivatives with Assay for Their Antitumor Activity," *Phosphorus, Sulfur, and Silicon*, 112: 7-17 (1996).

Gailani et al., "The role of the human homologue of *Drosophilia* patched in sporadic basal cell carcinomas," *Nature Genetics*, 14: 78-81 (1996).

Ghorab et al., "Synthesis and effect of some new [1,2,4]triazolo[4,3-a]quinazolin-5(4*H*)-ones and related compounds on Ehrlich Ascites Carcinoma cells," *Acta Pharm.*, 49: 1-10 (1999).

COMPOUNDS, COMPOSITIONS, AND METHODS

CROSS-REFERENCE TO RELATED APPLICATIONS

This application claims the benefit of co-pending provisional U.S. Application Ser. No. 60/414,756, filed Sep. 30, 2002 incorporated herein by reference.

FIELD OF THE INVENTION

This invention relates to quinazolinone-like derivatives that are inhibitors of the mitotic kinesin KSP and are useful in the treatment of cellular proliferative diseases, for example cancer, hyperplasias, restenosis, cardiac hypertrophy, immune disorders and inflammation.

BACKGROUND OF THE INVENTION

The mitotic spindle is responsible for distribution of replicate copies of the genome to each of the two daughter cells that result from cell division. Disruption of the mitotic spindle can inhibit cell division, and induce cell death. Microtubules are the primary structural element of the mitotic spindle; they are the site of action of certain existing therapeutic agents used to treat cancer, such as taxanes and vinca alkaloids. Microtubules, however, exist as elements in other types of cellular structures (including tracks for intracellular transport in nerve processes). The therapeutic targeting of microtubules can, therefore, modulate processes in addition to cellular proliferation, leading to side effects that limit the usefulness of such drugs.

Improvement in the specificity of agents used to treat cancer is of considerable interest because of the therapeutic benefits that would be realized if the side effects associated with the administration of these agents could be reduced. Dramatic improvements in the treatment of cancer have been associated with identification of therapeutic agents acting through novel mechanisms. Examples of this include not only the taxanes, but also the camptothecin class of topoisomerase I inhibitors.

One novel anti-proliferative mechanism entails selective inhibition of mitotic kinesins, enzymes that are essential for assembly and function of the mitotic spindle, but are not generally part of other microtubule structures, such as in nerve processes. See, e.g., Guidebook to the Cytoskeletal and Motor Proteins, Kreis and Vale, Eds., pp. 389-394 (Oxford University Press 1999). Mitotic kinesins play essential roles during all phases of mitosis. These enzymes are "molecular motors" that transform energy released by hydrolysis of ATP into mechanical force that drives the directional movement of cellular cargoes along microtubules. The catalytic domain sufficient for this task is a compact structure of approximately 340 amino acids. During mitosis, kinesins organize microtubules into the bipolar structure that is the mitotic spindle. Kinesins mediate movement of chromosomes along spindle microtubules, as well as structural changes in the mitotic spindle associated with specific phases of mitosis. Experimental perturbation of mitotic kinesin function causes malformation or dysfunction of the mitotic spindle, frequently resulting in cell cycle arrest and cell death. Mitotic kinesins are attractive targets for the discovery and development of novel anti-mitotic chemotherapeutics.

Among the mitotic kinesins that have been identified is KSP. KSP belongs to an evolutionarily conserved kinesin subfamily of plus end-directed microtubule motors that assemble into bipolar homotetramers consisting of antiparallel homodimers. During mitosis, KSP associates with microtubules of the mitotic spindle. Microinjection of antibodies directed against KSP into human cells prevents spindle pole separation during prometaphase, giving rise to monopolar spindles and causing mitotic arrest and induction of programmed cell death. KSP and related kinesins in other, non-human, organisms, bundle antiparallel microtubules and slide them relative to one another, thus forcing the two spindle poles apart. KSP may also mediate in anaphase B spindle elongation and focussing of microtubules at the spindle pole.

Human KSP (also termed HsEg5) has been described [Blangy, et al., Cell, 83:1159-69 (1995); Whitehead, et al., Arthritis Rheum., 39:1635-42 (1996); Galgio et al., J. Cell Biol., 135:339-414 (1996); Blangy, et al., J Biol. Chem., 272:19418-24 (1997); Blangy, et al., Cell Motil. Cytoskeleton, 40:174-82 (1998); Whitehead and Rattner, J. Cell Sci., 111:2551-61 (1998); Kaiser, et al., JBC 274:18925-31 (1999); GenBank accession numbers: X85137, NM004523 and U37426], and a fragment of the KSP gene (TRIP5) has been described [Lee, et al., Mol. Endocrinol., 9:243-54 (1995); GenBank accession number L40372]. *Xenopus* KSP homologs (Eg5), as well as *Drosophila* KLP61 F/KRP1 30 have been reported.

Recently, certain substituted quinazolinones have been described as inhibitors of mitotic kinesins for the treatment of cellular proliferative diseases (WO 01/30768 and WO 01/98278). It is an object of the present invention to provide novel inhibitors of mitotic kinesins such as KSP (particularly human KSP).

SUMMARY OF THE INVENTION

The present invention provides compounds, compositions and methods useful in the inhibition of mitotic kinesins, particularly KSP (more particularly human KSP). The compounds can be used to treat cellular proliferative diseases and include certain pyrrolidine- and piperidine-substituted quinazolinone derivatives.

In one aspect, the invention relates to one or more compounds selected from the group represented by Formula I:

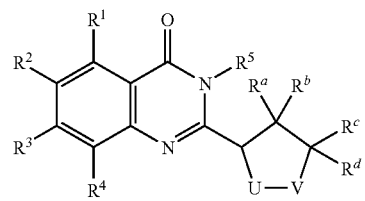

Formula I where:

U—V is chosen from —N($R^6$)—$CR^eR^f$—, —$CR^eR^f$—N($R^6$)—, —N($R^6$)—$CR^eR^f$—$CR^gR^h$—, —$CR^eR^f$—N($R^6$)—$CR^gR^h$, and —$CR^eR^f$—$CR^gR^h$—N($R^6$)—;

$R^a$, $R^b$, $R^c$, $R^d$, $R^e$, $R^f$, $R^g$ and $R^h$ are independently chosen from hydrogen, alkyl, aryl, aralkyl, heteroaryl, substituted alkyl, substituted aryl, substituted aralkyl, and substituted heteroaryl;

$R^1$, $R^2$, $R^3$, and $R^4$ are independently chosen from hydrogen, alkyl, alkoxy, halogen, cyano and substituted alkyl;

$R^5$ is chosen from alkyl, aryl, aralkyl, heteroaryl, heteroaralkyl, substituted alkyl, substituted aryl, substituted aralkyl, substituted heteroaryl and substituted heteroaralkyl; and R⁶ is chosen from hydrogen, acyl, alkyl, aryl, aralkyl, heteroaryl, substituted acyl, substituted alkyl, substituted aryl, substituted aralkyl and substituted heteroaryl;

including single stereoisomers, mixtures of stereoisomers, and pharmaceutically acceptable salts, solvates, and solvates of pharmaceutically acceptable salts thereof. Compounds of Formula I and pharmaceutically acceptable salts and solvates thereof are useful as active agents in the practice of the methods of treatment and in manufacture of compositions including the pharmaceutical formulations of the invention, and may also be useful as intermediates in the synthesis of such active agents.

In another aspect, the invention relates to one or more compounds selected from the group represented by Formula II:

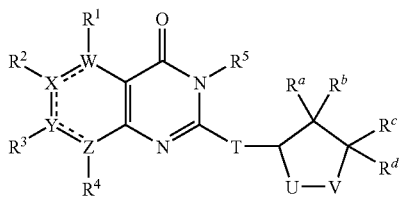

Formula II where:
T is a covalent bond or optionally substituted lower alkylene;
W, X and Y are independently chosen from —N=, N, —C=, CH, CR$^i$, O and S;
Z is chosen from —N=, N, —C=, CH, CR$^i$ or is absent, provided that:
no more than two of W, X, Y and Z are —N=, and
W, X or Y can be O or S only when Z is absent;
R$^i$ is chosen from alkyl, alkoxy, halogen, cyano and substituted alkyl; and
R¹ to R⁶, U and V are as defined with regard to Formula I, provided that R¹, R², R³ or R⁴ is absent where W, X, Y or Z, respectively, is —N=, O, S or absent;

including single stereoisomers, mixtures of stereoisomers, and pharmaceutically acceptable salts, solvates, and solvates of pharmaceutically acceptable salts thereof. The compounds encompassed by Formula II and pharmaceutically acceptable salts and solvates thereof will be seen to include those of Formula I; they are likewise useful as active agents in the practice of the methods of treatment and in manufacture of compositions including the pharmaceutical formulations of the invention, and may also be useful as intermediates in the synthesis of such active agents. The dashed lines in Formula II indicate that the corresponding bond may be a single bond (e.g., where X is CH) or a double bond (e.g., where X is —C=).

In one of its particular aspects the present invention pertains to a compound represented by Formula I or II, having a substituent selected from one or more of the following for R$^a$ to R$^h$, R¹ to R⁶, T, U, V, or W, X, Y and Z:
U—V is —N(R⁶)—CR$^e$R$^f$—CR$^g$R$^h$—;
R$^a$ to R$^h$ are chosen from hydrogen, lower alkyl (particularly methyl) and substituted lower alkyl;
R¹, R², R³ and R⁴ are independently chosen from hydrogen, halo (particularly chloro and fluoro), lower alkyl (particularly methyl), substituted lower alkyl, lower alkoxy (particularly methoxy), and cyano;

R⁵ is aralkyl or substituted aralkyl (particularly benzyl or substituted benzyl; most particularly benzyl);
R⁶ is acyl (particularly benzoyl), aryl (particularly phenyl), substituted aryl (particularly lower alkyl-, lower alkoxy-, and/or halo-substituted phenyl), aralkyl (particularly benzyl and phenylviny), heteroaralkyl, oxaaralkyl (particularly phenoxy lower alkyl), oxaheteroaralkyl, substituted acyl (particularly p-toluoyl), substituted aralkyl (particularly substituted benzyl and substituted phenylviny), substituted heteroaralkyl, substituted oxaaralkyl (particularly substituted phenoxy lower alkyl), or substituted oxaheteroaralkyl.
T is lower alkylene, substituted lower alkylene or a covalent bond (particularly a covalent bond); and
W, X, Y and Z are C= or —N=(particularly —C=).

Other particular aspects of the invention pertain to methods and to pharmaceutical formulations employing such a compound.

In one aspect, the invention relates to methods for treating cellular proliferative diseases, for disorders that can be treated by modulating KSP kinesin activity, and for inhibiting KSP kinesin by the administration of a therapeutically effective amount of a compound of Formula I or II, or a pharmaceutically acceptable salt or solvate of such compounds. Diseases and disorders that respond to therapy with compounds of the invention include cancer, hyperplasia, restenosis, cardiac hypertrophy, immune disorders and inflammation.

In another aspect, the invention relates to a pharmaceutical composition containing a therapeutically effective amount of a compound of Formula I or II or a pharmaceutically acceptable salt or solvate thereof admixed with at least one pharmaceutically acceptable excipient.

Yet another aspect of the invention relates to a kit having a compound, pharmaceutically acceptable salt or solvate of Formula I or II and a package insert or other labeling including directions for treating a cellular proliferative disease by administering an effective amount of the compound, salt or solvate. In one particular such aspect, the compound, pharmaceutically acceptable salt or solvate of Formula I or II is provided as a pharmaceutical composition.

In an additional aspect, the present invention provides methods of screening for compounds that will bind to a KSP kinesin, for example compounds that will displace or compete with the binding of the compounds of the invention. The methods entail combining a labeled compound of the invention, a KSP kinesin, and at least one candidate agent and determining the binding of the candidate agent to the KSP kinesin.

In a further aspect, the invention provides methods of screening for modulators of KSP kinesin activity. The methods entail combining a compound of the invention, a KSP kinesin, and at least one candidate agent and determining the effect of the candidate agent on the KSP kinesin activity.

DETAILED DESCRIPTION OF THE INVENTION

The present invention provides compounds, compositions and methods useful in the inhibition of mitotic kinesins, particularly KSP (more particularly human KSP). The compounds can be used to treat cellular proliferative diseases and include certain pyrrolidine- and piperidine-substituted quinazolinone derivatives. The invention further relates to pharmaceutical formulations comprising compounds of the invention, and methods of treatment employing such compounds or compositions.

Definitions

As used in the present specification, the following words and phrases are generally intended to have the meanings as set forth below, except to the extent that the context in which they are used indicates otherwise. The following abbreviations and terms have the indicated meanings throughout:

Ac=acetyl
Boc=t-butyloxy carbonyl
c-=cyclo
CBZ=carbobenzoxy=benzyloxycarbonyl
DCM=dichloromethane=methylene chloride=$CH_2Cl_2$
DMF=N,N-dimethylformamide
DMSO=dimethyl sulfoxide
Et=ethyl
PyBroP=bromo-tris-pyrrolidinophosphonium hexafluorophosphate
s-=secondary
t-=tertiary
TFA=trifluoroacetic acid The substituents identified as U, V, W and Y are intended to have the meanings set forth in the Summary, this Detailed Description and the Claims; they are not intended to designate the atomic elements Uranium, Vanadium, Tungsten and Yttrium.

The term "optional" or "optionally" means that the subsequently described event or circumstance may or may not occur, and that the description includes instances where said event or circumstance occurs and instances in which it does not. For example, "optionally substituted alkyl" includes "alkyl" and "substituted alkyl," as defined below. It will be understood by those skilled in the art with respect to any group containing one or more substituents that such groups are not intended to introduce any substitution or substitution patterns that are sterically impractical, synthetically non-feasible and/or inherently unstable.

"Alkyl" is intended to include linear, branched, or cyclic aliphatic hydrocarbon structures and combinations thereof, which structures may be saturated or unsaturated (particularly having up to 20 carbon atoms, more particularly up to $C_{13}$.). Lower alkyl refers to alkyl groups of from 1 to 5 (particularly 1 to 4) carbon atoms. Examples of lower alkyl groups include methyl, ethyl, propyl, isopropyl, butyl, s-and t-butyl and the like. Cycloalkyl (or carbocyclic) is a subset of alkyl and includes cyclic aliphatic hydrocarbon groups of from 3 to 13 carbon atoms. Examples of cycloalkyl groups include c-propyl, c-butyl, c-pentyl, norbornyl, adamantyl and the like. In this application, alkyl refers to alkanyl, alkenyl and alkynyl residues; it is intended to include cyclohexylmethyl, vinyl, allyl, isoprenyl and the like. Alkylene, alkenylene and alkynylene are other subsets of alkyl, referring to the same residues as alkyld but having two points of attachment. Examples of alkylene include ethylene ($-CH_2CH_2-$), ethenylene ($-CH=CH-$), propylene ($-CH_2CH_2CH_2-$), dimethylpropylene ($-CH_2C(CH_3)_2CH_2-$) and cyclohexylpropylene ($-CH_2CH_2CH(C_6H_{13})-$). When an alkyl residue having a specific number of carbons is named, all geometric isomers of that residue having the specified number of carbons are meant to be included; thus, for example, "butyl" is meant to include n-butyl, sec-butyl, isobutyl and t-butyl; "propyl" includes n-propyl and isopropyl.

The term "alkoxy" or "alkoxyl" refers to the group —O-alkyl, particularly including from 1 to 8 carbon atoms in a straight, branched or cyclic configuration, or combinations thereof, attached to the parent structure through an oxygen. Examples include methoxy, ethoxy, propoxy, isopropoxy, cyclopropyloxy, cyclohexyloxy and the like. Lower-alkoxy refers to groups containing one to five carbons.

The term "substituted alkoxy" refers to the group —O-(substituted alkyl). One particular substituted alkoxy group is "polyalkoxy" or —O-(optionally substituted alkylene)-(optionally substituted alkoxy), and includes groups such as —$OCH_2CH_2OCH_3$, and glycol ethers such as polyethyleneglycol and —$O(CH_2CH_2O)_xCH_3$, where x is an integer of about 2-20, particularly about 2-10, and more particularly about 2-5. Another particular substituted alkoxy group is hydroxyalkoxy or $OCH_2(CH_2)_yOH$, where y is an integer of about 1-10, particularly about 1-4.

"Acyl" refers to groups of from 1 to 8 carbon atoms in a straight, branched or cyclic configuration, or combinations thereof, or to a hydrogen atom attached to the parent structure through a carbonyl functionality. Such groups may be saturated or unsaturated, and aliphatic or aromatic. One or more carbons in the acyl residue may be replaced by nitrogen, oxygen or sulfur as long as the point of attachment to the parrent remains at the carbonyl. Examples include formyl, acetyl, benzoyl, propionyl, isobutyryl, t-butoxycarbonyl, benzyloxycarbonyl, aminocarbonyl, and the like. Lower-acyl refers to an acyl group containing one to five carbons. "Substituted acyl" refers to an acyl group where one or more of the hydrogens otherwise attached to a carbon, nitrogen or sulfur atom is substituted, the point of attachment to the parent moiety remaining at the carbonyl.

The term "acyloxy" refers to the group —O-acyl. "Substituted acyloxy" refers to the group —O-substituted acyl.

The term "amidino" refers to the group —C(=NH)—$NH_2$. The term "substituted amidino" refers to the formula —C(=NR)—NRR in which each R is independently selected from the group:

hydrogen, optionally substituted alkyl, optionally substituted alkoxy, optionally substituted aminocarbonyl, optionally substituted aryl, optionally substituted heteroaryl, optionally substituted heterocyclyl, acyl, alkoxycarbonyl, sulfanyl, sulfinyl and sulfonyl, provided that at least one R is not hydrogen.

The term "amino" refers to the group —$NH_2$. The term "substituted amino" refers to the group —NHR or —NRR where each R is independently selected from the group: optionally substituted acyl, optionally substituted alkyl, optionally substituted alkoxy, optionally substituted amino, optionally substituted aryl, optionally substituted heteroaryl, optionally substituted heterocyclyl, sulfinyl and sulfonyl, e.g., methylamino, dimethylamino, diethylamino, methylsulfonylamino, furanyl-oxy-sulfonamino, guanidino.

"Aryl" and "heteroaryl" mean a 5- or 6-membered aromatic ring or heteroaromatic ring containing 1-4 heteroatoms selected from O, N, or S; a bicyclic 9- or 10-membered aromatic ring system or heteroaromatic ring system containing 1-4 (or more) heteroatoms selected from O, N, or S; or a tricyclic 13- or 14-membered aromatic ring system or heteroaromatic ring system containing 1-4 (or more) heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole; particularly imidazole and imidazoline.

"Aralkyl" refers to a residue in which an aryl moiety is attached to the parent structure via an alkyl residue. Examples include benzyl, phenethyl, phenylvinyl, phenylallyl and the like. "Heteroaralkyl" refers to a residue in which a heteroaryl moiety is attached to the parent structure via an alkyl residue. Examples include furanylmethyl, pyridinylmethyl, pyrimidinylethyl and the like.

The term "aryloxy" refers to the group —O-aryl. Similarly; "aralkoxy" and "heteroaralkoxy" refer, respectively, to an aryl or heteroaryl moiety attached to the parent structure via an alkoxy residue.

"Halogen" or "halo" refers to fluorine, chlorine, bromine or iodine (particularly fluorine, chlorine and bromine). Dihaloaryl, dihaloalkyl, trihaloaryl etc. refer to aryl and alkyl substituted with a plurality of halogens, but not necessarily a plurality of the same halogen; thus 4-chloro-3-fluorophenyl is within the scope of dihaloaryl.

"Heterocycle" or "heterocyclyl" means a cycloalkyl or aryl residue in which one to four of the carbons is replaced by a heteroatom such as oxygen, nitrogen or sulfur (i.e., encompassing heterocydoalkyl and heteroaryl). Examples of heterocyclyl residues that fall within the scope of the invention include imidazolyl, imidazolinyl, pyrrolidinyl, pyrazolyl, pyrrolyl, indolyl, quinolinyl, isoquinolinyl, tetrahydroisoquinolinyl, benzofuranyl, benzodioxanyl, benzodioxolyl (commonly referred to as methylenedioxyphenyl, when occurring as a substituent), tetrazolyl, morpholinyl, thiazolyl, pyridinyl, pyridazinyl, pyrimidinyl, thiophenyl, furanyl, oxazolyl, oxazolinyl, isoxazolyl, dioxanyl, tetrahydrofuranyl and the like. "N-heterocyclyl" refers to a nitrogen-containing heterocycle as a substituent residue. Examples of N-heterocyclyl residues include 4-morpholinyl, 4-thiomorpholinyl, 1-piperidinyl, 1-pyrrolidinyl, 3-thiazolidinyl, piperazinyl and 4-(3,4-dihydrobenzoxazinyl). Examples of substituted heterocyclyl include 4-methyl-1-piperazinyl and 4-benzyl-1-piperidinyl.

The terms "heteroaryloxy" and "heterocyclooxy" refer, respectively to the groups —O-heteroaryl and —O-heterocyclyl.

The term "solvate" refers to a compound (e.g., a compound of Formula I or II or a pharmaceutically acceptable salt thereof) in physical association with one or more molecules of a pharmaceutically acceptable solvent. It will be understood that phrases such as "a compound of Formula I or II or a pharmaceutically acceptable salt or solvate thereof" are intended to encompass the compound of Formula I or II, a pharmaceutically acceptable salt of the compound, a solvate of the compound, and a solvate of a pharmaceutically acceptable salt of the compound.

The term "substituted" as used with regard to alkyl, aryl, aralkyl, heteroaryl and heterocyclyl refers to an alkyl, aryl, aralkyl, heteroaryl or heterocyclyl moiety wherein one or more (up to about 5, particularly up to about 3) hydrogen atoms are replaced by a substituent independently selected from the group: optionally substituted acyl (e.g., aminocarbonyl and alkoxycarbonyl or "esters"), optionally substituted acyloxy (e.g., acid esters, carbamic acid esters, carbonic acid esters, and thiocarbonic acid esters), optionally substituted alkyl (e.g., fluoroalkyl), optionally substituted alkoxy (e.g., methoxy and methoxymethoxy), alkylenedioxy (e.g. methylenedioxy), optionally substituted amino (e.g., alkylamino, dialkylamino, carbonylamino, benzyloxycarbonylamino or "CBZ-amino", and carboxamido), optionally substituted amidino, optionally substituted aryl (e.g., phenyl and 4-methyl-phenyl or "tolyl"), optionally substituted aralkyl (e.g., benzyl), optionally substituted aryloxy (e.g., phenoxy), optionally substituted aralkoxy (e.g., benzyloxy), optionally substituted heteroaryl, optionally substituted heteroaralkyl, optionally substituted heteroaryloxy, optionally substituted heteroaralkoxy, carboxy (—COOH), cyano, halogen, hydroxy, nitro, sulfanyl, sulfinyl, sulfonyl and thio. In the compounds of Formula II where T is substituted alkylene, the term "substituted" also refers to alkylene groups where one or more (up to about 3, particularly 1) carbon atoms are replaced by a heteroatom independently selected from O, N or S, such as —$CH_2$—S—$CH_2$—.

The term "sulfanyl" refers to the groups: —S-(optionally substituted alkyl), —S-(optionally substituted aryl), —S-(optionally substituted heteroaryl), and —S-(optionally substituted heterocyclyl).

The term "sulfinyl" refers to the groups: —S(O)—H, —S(O)-(optionally substituted alkyl), —S(O)-(optionally substituted amino), —S(O)-(optionally substituted aryl), —S(O)-(optionally substituted heteroaryl), and —S(O)-(optionally substituted heterocyclyl).

The term "sulfonyl" refers to the groups: —$S(O_2)$—H, —$S(O_2)$-(optionally substituted alkyl), —$S(O_2)$-(optionally substituted amino), —$S(O_2)$-(optionally substituted aryl), —$S(O_2)$-(optionally substituted heteroaryl), —$S(O_2)$-(optionally substituted heterocyclyl), —$S(O_2)$-(optionally substituted alkoxy), —$S(O_2)$-optionally substituted aryloxy), —$S(O_2)$-(optionally substituted heteroaryloxy), and —$S(O_2)$-(optionally substituted heterocyclyloxy).

"Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(.±.)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown are designated (+) or (−) depending on the direction (dextro- or levorotatory) which they rotate plane polarized light at the wavelength of the sodium D line. The term "substantially pure" means having at least about 95% chemical purity with no single impurity greater than about 1%. The term "substantially optically pure" or "substantially enantiomerically pure" means having at least about 95% enantiomeric excess. The invention contemplates the use of pure enantiomers and mixtures of enantiomers, including racemic mixtures, although the use of a substantially optically pure enantiomer will generally be most suitable.

"Mitotic spindle formation" refers to the organization of microtubules into bipolar structures by mitotic kinesins. "Mitotic spindle dysfunction" refers to mitotic arrest, monopolar spindle formation or mitotic spindle malformation, in which context "malformation" encompasses the splaying of mitotic spindle poles, or otherwise causing morphological perturbation of the mitotic spindle. The term "inhibit" as used with reference to mitotic spindle formation, means altering mitotic spindle formation, including decreasing spindle formation, and increasing or decreasing spindle pole separation. "Anti-mitotic" means inhibiting or having the potential to inhibit mitosis, for example, as described above.

The term "pharmaceutically acceptable salts" is meant to include both acid and base addition salts. A "pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, or organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly suitable are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The term "therapeutically effective amount" or "effective amount" refers to that amount of a compound of Formula I or II that is sufficient to effect treatment, as defined below, when administered to a patient in need of such treatment. The effective amount will vary depending upon the patient and disease condition being treated, the weight and age of the patient, the severity of the disease condition, the particular compound, pharmaceutically acceptable salt or solvate of Formula I or II chosen, the dosing regimen to be followed, timing of administration, the manner of administration and the like, all of which can readily be determined by one of ordinary skill in the art. In a particular aspect of the invention, the effective amount will be an amount sufficient to inhibit KSP kinesin activity in cells involved with the disease being treated.

The term "treatment" or "treating" means any treatment of a disease in a patient, including:

a) preventing the disease, that is, causing the clinical symptoms of the disease not to develop;

b) inhibiting the disease, that is, slowing or arresting the development of clinical symptoms; and/or c) relieving the disease, that is, causing the regression of clinical symptoms.

A "patient" for the purposes of the present invention includes humans and other animals, particularly mammals, and other organisms. Thus the methods are applicable to both human therapy and veterinary applications. In a particular embodiment the patient is a mammal, most particularly the patient is human.

COMPOUNDS OF THE PRESENT INVENTION

The present invention provides certain quinazolinone derivatives. The compounds are inhibitors of one or more mitotic kinesins. The present invention capitalizes on the finding that perturbation of mitotic kinesin function causes malformation or dysfunction of mitotic spindles, frequently resulting in cell cycle arrest and cell death.

Accordingly, the present invention relates to one or more compounds selected from the group represented by Formula I:

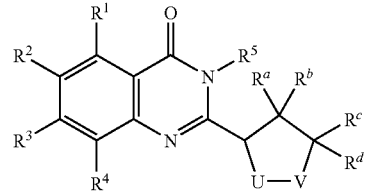

Formula I where:
U—V is chosen from —N(R$^6$)—CR$^e$R$^f$—, —CR$^e$R$^f$—N(R$^6$)—, —N(R$^6$)—CR$^e$R$^f$—CR$^9$R$^h$—, —CR$^e$R$^f$—N(R$^6$)—CR$^9$R$^h$—, and —CR$^e$R$^f$—CR$^9$R$^h$—N(R$^6$)—;

R$^a$, R$^b$, R$^c$, R$^d$, R$^e$, R$^f$, R$^g$ and R$^h$ are independently chosen from hydrogen, alkyl, aryl, aralkyl, heteroaryl, substituted alkyl, substituted aryl, substituted aralkyl and substituted heteroaryl;

R$^1$, R$^2$, R$^3$, and R$^4$ are independently chosen from hydrogen, alkyl, alkoxy, halogen, cyano and substituted alkyl;

R$^5$ is chosen from alkyl, aryl, aralkyl, heteroaryl, heteroaralkyl, substituted alkyl, substituted aryl, substituted aralkyl, substituted heteroaryl and substituted heteroaralkyl; and R$^6$ is chosen from hydrogen, acyl, alkyl, aryl, aralkyl, heteroaryl, substituted acyl, substituted alkyl, substituted aryl, substituted aralkyl and substituted heteroaryl;

including single stereoisomers, mixtures of stereoisomers, and pharmaceutically acceptable salts, solvates, and solvates of pharmaceutically acceptable salts thereof.

In another aspect, the invention relates to one or more compounds selected from the group represented by Formula II:

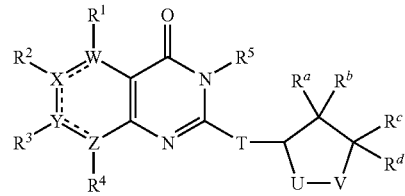

Formula II where:
T is a covalent bond or optionally substituted lower alkylene;

W, X and Y are independently chosen from —N═, N, —C═, CH, CR$^i$, O and S;

Z is chosen from —N═, N, —C═, CH, CR$^i$ or is absent, provided that:
no more than two of W, X, Y and Z are —N═, and
W, X or Y can be O or S only when Z is absent;

R$^i$ is chosen from alkyl, alkoxy, halogen, cyano and substituted alkyl; and

R$^1$ to R$^6$, U and V are as defined with regard to Formula I, provided that R$^1$, R$^2$, R$^3$ or R$^4$ is absent where W, X, Y or Z, respectively, is —N═, O, S or absent;

including single stereoisomers, mixtures of stereoisomers, and the pharmaceutically acceptable salts, solvates, and solvates of pharmaceutically acceptable salts thereof. The compounds encompassed by Formula II will be seen to include those of Formula I; they are likewise useful as active agents in the practice of the methods of treatment and in manufacture of compositions including the pharmaceutical formulations of the invention, and may also be useful as intermediates in the synthesis of such active agents. The dashed lines in Formula II indicate that the corresponding bond may be a single bond (e.g., where X is CH) or a double bond (e.g., where X is C=). For the sake of simplicity in the following description and claims, substituents T, U, W, X, Y and Z will not be discussed in connection with certain compounds falling within the scope of Formula I.

Many of the compounds described herein contain one or more asymmetric centers and may thus give rise to enantiomers, diastereomers, and other stereoisomeric forms that may be defined, in terms of absolute stereochemistry, as (R)— or (S)—. When the compounds described herein contain olefinic double bonds or other centers of geometric asymmetry, and unless specified otherwise, it is intended that such compounds include both E and Z geometric isomers. All tautomeric forms are also intended to be included. The present invention is meant to include all such possible isomers, including racemic mixtures, intermediate mixtures, optically pure forms, substantially optically pure forms, enantiomerically pure forms, and substantially enantiomerically pure forms.

Nomenclature

The compounds of Formula I and II can be named and numbered (e.g., using AutoNom version 2.1 in ISIS-DRAW or ChemDraw) as described below.

For example, the compound of Formula IA:

Formula IA i.e., the compound according to Formula I where U—V is —N(R$^6$)—CR$^e$R$^f$—; R$^1$, R$^2$, R$^4$, and R$^a$ to R$^f$ are H; R$^3$ is chloro; R$^5$ is benzyl; and R$^6$ is p-methyl-benzoyl, can be named 3-benzyl-7-chloro-2-[1-(4-methyl-benzoyl)-pyrrolidin-2-yl]-3H-quinazolin-4-one.

The compound of Formula IB:

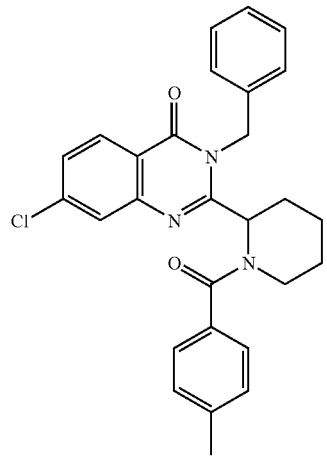

Formula IB i.e., the compound according to Formula I where U—V is —N(R$^6$)—CR$^e$R$^f$—CR$^g$R$^h$—; R$^1$, R$^2$, R$^4$ and R$^a$ to R$^h$ are H; R$^3$ is chloro; R$^5$ is benzyl; and R$^6$ is p-methyl-benzoyl, can be named 3-benzyl-7-chloro-2-[1-(4-methyl-benzoyl)-piperidin-2-yl]-3H-quinazolin-4-one.

The compound of Formula IC:

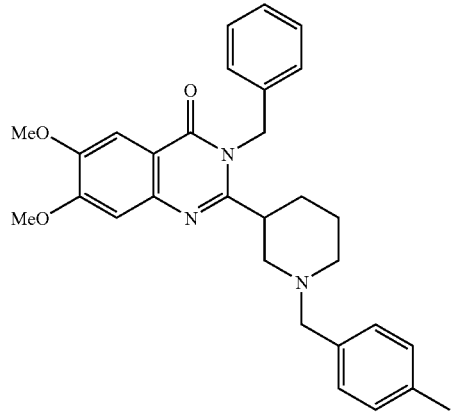

Formula IC i.e., the compound according to Formula I where U—V is —CR$^e$R$^f$—N(R$^6$)—CR$^g$R$^h$—; R$^1$, R$^4$, and R$^a$ to R$^h$ are H; R$^2$ and R$^3$ are methoxy; R$^5$ is benzyl; and R$^6$ is p-methyl-benzyl, can be named 3-benzyl-6,7-dimethoxy-2-[1-(4-methyl-benzyl)-piperidin-3-yl]-3H-quinazolin-4-one.

The compound of Formula ID:

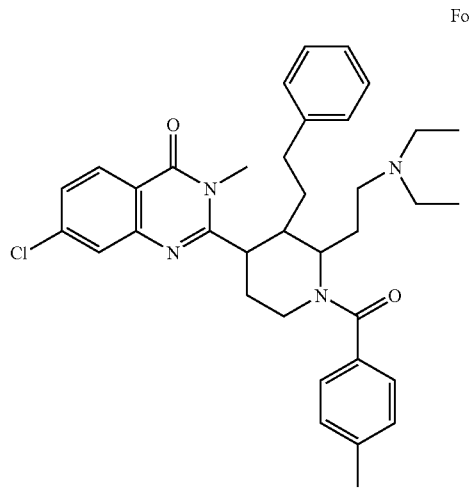

Formula ID i.e., the compound according to Formula I where U—V is —CR$^e$R$^f$—CR$^g$R$^h$—N(R$^6$)—; R$^1$, R$^2$, R$^4$, R$^b$ and R$^d$ to R$^h$ are H; R$^3$ is chloro; R$^5$ is methyl; R$^a$ is phenethyl; R$^c$ is diethylamino-ethyl; and R$^6$ is p-methyl-benzoyl, can be named 7-chloro-2-[2-(2-diethylamino-ethyl)-1-(4-methyl-benzoyl)-3-phenethyl-piperidin-4-yl]-3-methyl-3H-quinazolin-4-one.

The compound of Formula IIA:

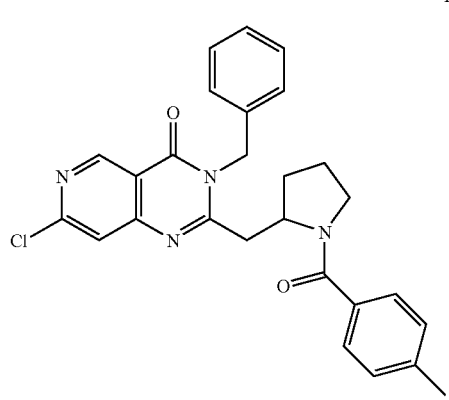

Formula IIA i.e., the compound according to Formula II where T is methylene; U—V is —N(R$^6$)—CR$^e$R$^f$—; W, Y and Z are —C═; X is —N═; R$^1$, R$^4$ and R$^a$ to R$^f$ are H; R$^2$ is absent; R$^3$ is chloro; R$^5$ is benzyl; and R$^6$ is p-methyl-benzoyl, can be named 3-benzyl-7-chloro-2-[1-(4-methyl-benzoyl)-pyrrolidin-2-ylmethyl]-3H-pyrido[4,3-d]pyrimidin-4-one.

The compound of Formula IIB:

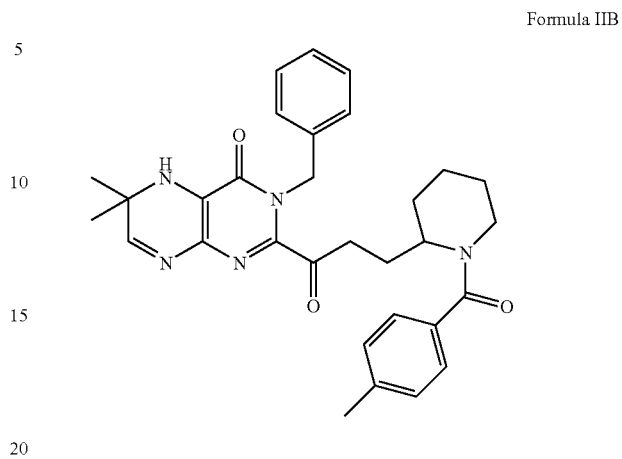

Formula IIB i.e., the compound according to Formula I where the dashed line between W and X is a single bond, T is 3-propionyl; U—V is —N(R$^6$)—CR$^e$R—CR$^g$R$^h$—; W is N; X is CR$^i$ where R$^i$ is methyl; Y is CH; Z is ═N—; R$^1$, R$^4$ and R$^a$ to R$^h$ are H; R$^2$ is methyl; R$^3$ is absent; R$^5$ is benzyl; and R$^6$ is p-methyl-benzoyl, can be named 3-benzyl-6,6-dimethyl-2-3-[1-(4-methyl-benzoyl)-piperidin-2-yl]-propionyl}-5,6-dihydro-3H-pteridin-4-one.

The compound of Formula IIC:

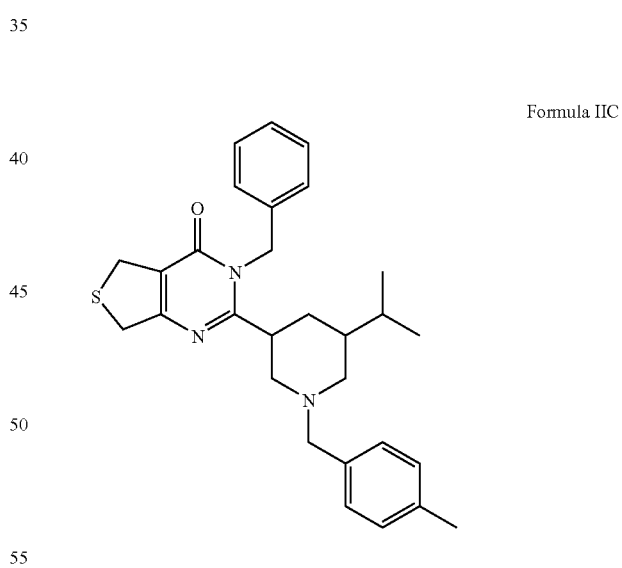

Formula IIC i.e., the compound according to Formula II where the dashed lines are single bonds, T is absent; U—V is —CR$^e$R$^f$—N(R$^6$)—CR$^g$R$^h$; Z, R$^2$ and R$^4$ are absent; W and Y are CH; X is S; R$^1$, R$^3$, and R$^a$, R$^b$, and R$^d$ to R$^h$ are H; R$^c$ is isopropyl; R$^5$ is benzyl; and R$^6$ is p-methyl-benzyl, can be named 3-benzyl-2-[5-isopropyl-1-(4-methyl-benzyl)-piperidin-3-yl]-5,7-dihydro-3H-thieno[3,4-d]pyrimidin-4-one.

The compound of Formula IID:

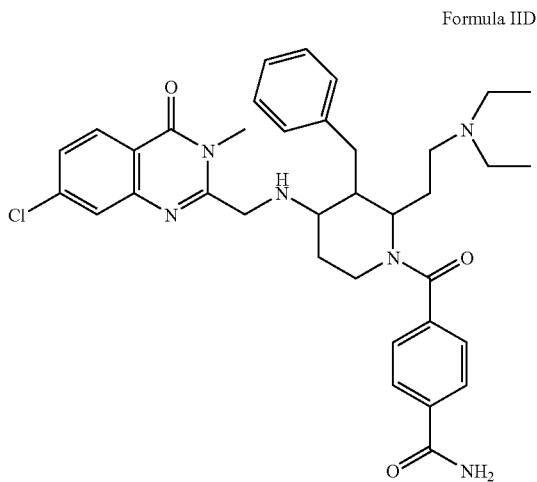

Formula IID i.e., the compound according to Formula II where T is aminomethylene; U—V is —CR$^e$R$^f$—CR$^g$R$^h$—N(R$^6$)—; R$^1$, R$^2$, R$^4$, R$^b$ and R$^d$ to R$^h$ are H; R$^3$ is chloro; R$^5$ is methyl; R$^a$ is benzyl; R$^c$ is diethylamino-ethyl; and R$^6$ is p-carbonyl-benzamide, can be named 4-[3-benzyl-4-[(7-chloro-3-methyl-4-oxo-3,4-dihydro-quinazolin-2-ylmethyl)-amino]-2-(2-diethylamino-ethyl)-piperidine-1-carbonyl-benzamide.

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can, of course, also be used.

When desired, the (R)— and (S)-isomers may be resolved by methods known to those skilled in the art, for example by formation of diastereoisomeric salts or complexes which may be separated, for example, by crystallisation; via formation of diastereoisomeric derivatives which may be separated, for example, by crystallisation, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. For example, a compound of Formula I or II can be dissolved in a lower alkanol and placed on a Chiralpak AD (205×20 mm) column (Chiral Technologies, Inc.) conditioned for 60 min at 70% EtOAc in Hexane. It will be appreciated that where the desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents, or by converting one enantiomer to the other by asymmetric transformation.

Synthesis of the Compounds of Formula I and II

Brief Description of Reaction Schemes

Syntheses of the compounds of Formula I and II are described below with reference to Reaction Schemes 1 and 2.

Reaction Scheme 1 illustrates a synthesis of the compounds of Formulae I and II [excluding the 2-(piperidin-2-yl)-3-quinazolin-4-ones]. The nitrogen atom of U—V is protected until cyclization, followed by de-protection and derivatization to provide R$^6$ substituents other than hydrogen.

Reaction Scheme 2 depicts a synthesis for the compounds of Formulae I and II [including 2-(piperidin-2-yl)-3H-quinazolin-4-ones], illustrating the synthesis of compounds where R$^6$ is acyl.

It will be appreciated by those skilled in the art that one or more of the reactants, steps and/or conditions described with reference to Reaction Schemes 1 and 2 may require adjustment to accommodate non-hydrogen substituents, e.g., at R$^1$ to R$^6$ and R$^a$ to R$^h$.

Starting Materials

The N-protected pyrrolidine and piperidine dicarboxylic acids of Formula 101 (e.g., pyrrolidine-1,2-dicarboxylic acid 1-tert-butyl ester), the anthranilic acids of Formula 102 (e.g., 4-chloro-anthranilic acid) and other reactants are commercially available, e.g., from Aldrich Chemical Company, Milwaukee, Wisc. or may be readily prepared by those skilled in the art using commonly employed synthetic methodology.

Reaction Scheme 1

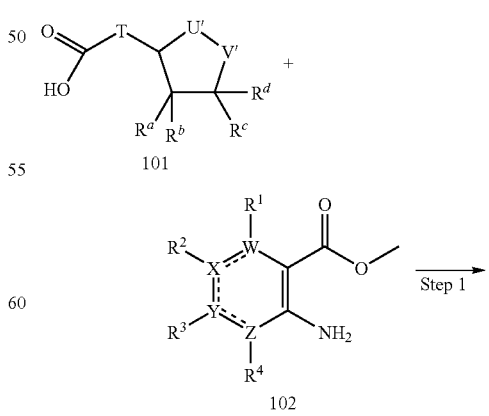

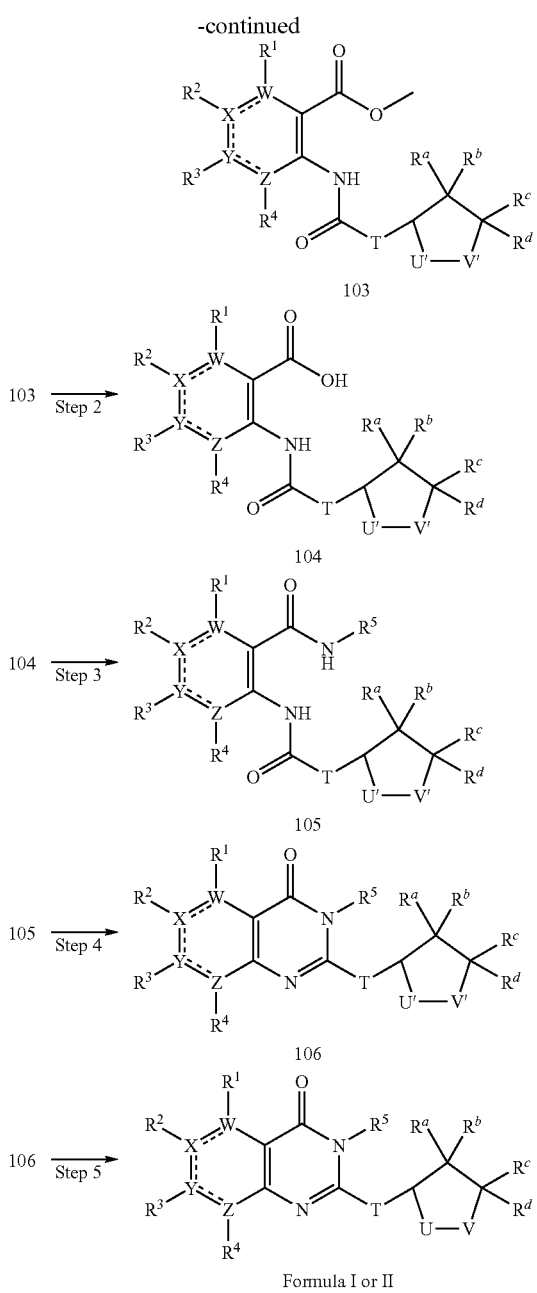

Formula I or II

Referring to Reaction Scheme 1, the $R^6$ component of "U—V" is not specifically shown. In Formulae 102 to 106 the $R^6$ moiety is a protecting group. In the end products of Step 5 (Formula I or II) $R^6$ is as defined, initially being hydrogen upon de-protection of U—V and optionally being further derivatized. Products where $R^6$ is aryl or heteroaryl can be obtained by starting with the corresponding arylated compound of Formula 101 or by a palladium catalyzed arylation (e.g., as described by Wolfe, J. P.; Tomori, H; Sadighi, J. P.; Yin, J.; and Buchwald, S. L., J. Org. Chem., 2000, 65, 1158-1174) of a de-protected product of Step 5 where $R^6$ is hydrogen.

Preparation of Formula 103 Referring to Reaction Scheme 1, Step 1, a solution is made of an optionally substituted o-amino alicyclic, heterocyclic or (hetero)aryl acid of Formula 102 (such as anthranilic acid), a slight molar excess of an N-protected pyrrolidine- or piperidine-dicarboxylic acid of Formula 101 [where U'—V' is —N($R^{6'}$)—CR$^e$R$^f$—, —CR$^e$R$^f$—N($R^{6'}$)—, —CR$^e$R$^f$—N($R^{6'}$)—CR$^g$R$^h$— or —CR$^e$R$^f$—CR$^g$R$^h$—N($R^{6'}$)—, and $R^{6'}$ is an amino-protecting group, such as Fmoc and Boc] and a slight molar excess of PyBroP dissolved in an organic solvent (e.g., diisopropylethylamine in pyridine). The solution is stirred for 12 to 20 hours at room temperature to afford the corresponding compound of Formula 103, which is conventionally isolated and purified.

Preparation of Formula 104 Referring to Reaction Scheme 1, Step 2, a compound of Formula 103 is dissolved in an organic solvent (e.g., a lower alkanol such as ethanol) and treated with an aqueous hydroxide (e.g., NaOH aq. solution). The mixture is stirred at room temperature for 12 to 20 hours and then concentrated under vacuum. The residue is washed (e.g., with saturated NaCl and concentrated phosphoric acid) and then extracted (e.g., with dichloromethane). Conventional isolation and purification affords the corresponding acid of Formula 104.

Preparation of Formula 105 Referring to Reaction Scheme 1, Step 3, to a solution of Formula 104 in an organic solvent (e.g., dichloromethane) is added large molar excesses of EDC and diisopropylethylamine. After stirring at room temperature for 1 to 2 hours, a large molar excess of an amine of formula $H_2N$—$R^5$ (such as benzylamine) is added and the reaction is stirred for an additional 24 to 60 hours. The mixture is washed, dried and isolated to afford the corresponding di-carbamoyl compound of Formula 105, and may include a small amount of the corresponding cyclized compound of Formula 106, which is taken forward without further purification.

Preparation of Formula 106 Referring to Reaction Scheme 1, Step 4, a compound of Formula 105 (optionally in the presence of a compound of Formula 106) is stirred in ethylene glycol with $K_2CO_3$ at 120° C. for 12 to 20 hours, allowed to cool to room temperature, and is extracted (e.g., with dichloromethane). The organic fractions are conventionally isolated and purified to afford the pure cyclized compound of Formula 106.

Preparation of Formula I or II where $R^6$ is Hydrogen Referring to Reaction Scheme 1, Step 5, a solution of Formula 106 where $R^{6'}$ of U'—V' is a Boc group, is treated with a 1:1 mixture of TFA/dichloromethane for 30 minutes to 2 hours at room temperature. The solution is concentrated under vacuum and partitioned (e.g., between dichloromethane and saturated $NaHCO_3$). The aqueous layer is extracted (e.g., with dichloromethane) and the combined organic layers are conventionally isolated to afford the corresponding de-protected pyrrolidinyl- or piperidinyl product of Formula I or II, which can be purified or taken forward without further purification.

Preparation of Formula I or II where $R^6$ is Acyl To a solution of Formula I or II where $R^6$ is hydrogen in an organic solvent (e.g,. dichloromethane) is added large molar excesses of an acyl halide (e.g., toluoyl chloride) and diisopropylethylamine. The mixture is stirred for 30 minutes to 2 hours and then partitioned (e.g., between saturated $NaHCO_3$ and ethyl acetate). Conventional isolation and purification of the organic phase affords the corresponding compound of Formula I or II where $R^6$ is acyl.

Preparation of Formula I where $R^6$ is Optionally Substituted Alkyl, Optionally Substituted Aralkyl or Optionally Sutstituted Heteroaralkyl To a solution of Formula I or II where $R^6$ is hydrogen in an organic solvent (e.g,. dichloromethane) is added a slight molar excess of an aldehyde comprising $R^{6''}$ (i.e., a compound having formula $R^{6''}$—CHO where $R^{6''}$—$CH_2$— is equivalent to $R^6$ and $R^6$ is as described above; e.g., fptolualdehyde) and a large molar excess of NaHB(OAc)₃. The mixture is stirred for 30 minutes to 1 hour at room temperature. The reaction is quenched with saturated NaHCO₃ and the aqueous phase extracted (e.g., with dichloromethane). Conventional isolation and purification of the organic phase affords the corresponding compound of Formula I or II where $R^6$ is optionally substituted-alkyl, -aralkyl or -heteroaralkyl.

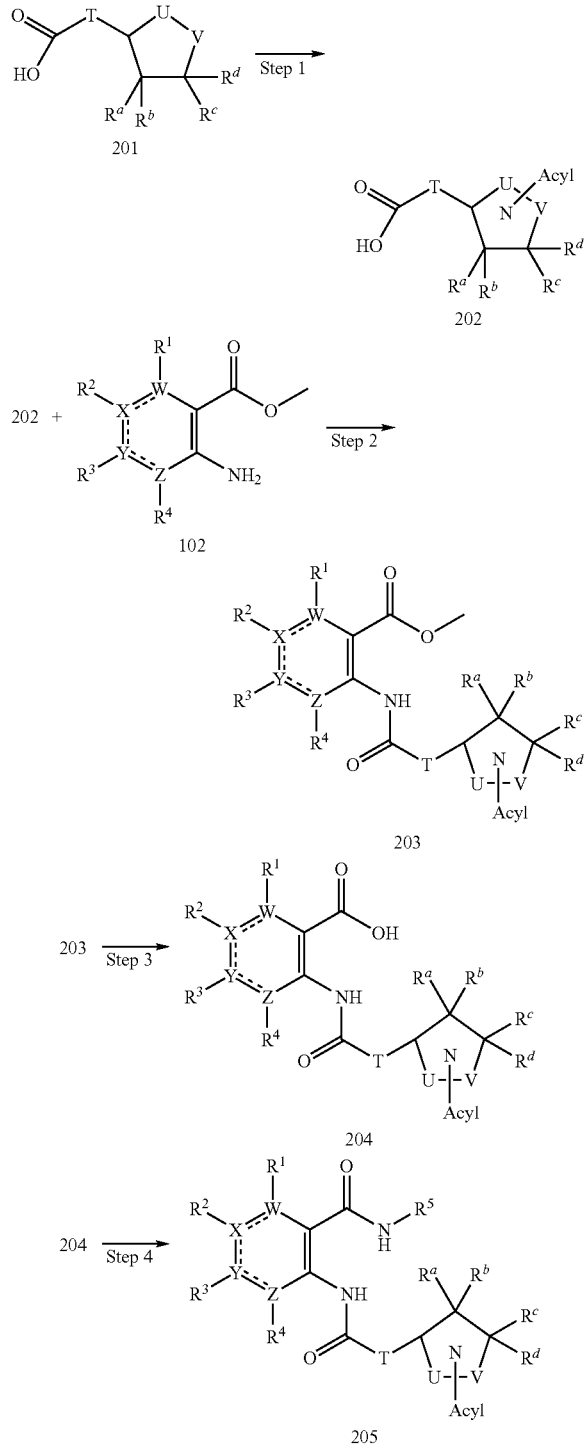

Reaction Scheme 2

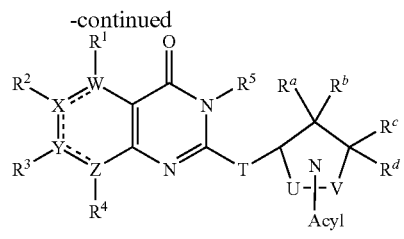

Formula I or II

Referring to Reaction Scheme 2, in Formula 201 the $R^6$ moiety of "U—V" is hydrogen. In Formulae 202 through 205 and in Formulae I and II, the "N-Acyl" moiety represents the —N($R^6$)— portion of "U—V" where $R^6$ is Acyl.

Preparation of Formula 202 Referring to Reaction Scheme 2, Step 1, a slight molar excess of an acyl halide (e.g., p-toluoyl chloride) is slowly added, portionwise, to a 0° C. solution of a pyrollidine- or piperidine-mrboxylic acid of Formula 201 in 2M NaOH. The mixture is stirred for an additional 30 minutes to 2 hours at room temperature, cooled to 0° C., and partitioned (e.g., between 1N HCl and dichloromethane). The organic layer is isolated and purified to afford the corresponding N-acyl-pyrollidine- or -piperidine-carboxylic acid of Formula 202.

Preparation of Formula 203 Referring to Reaction Scheme 2, Step 2, a compound of Formula 102 is combined with a slight molar excess of a compound of Formula 202, and one-fifth molar equivalents each of PyBroP and diisopropylethylamine in DMF. The reaction takes place at −15° C. with stirring for 12 to 20 hours, allowing the temperature to rise to room temperature. The product is isolated and purified to afford the corresponding compound of Formula 203.

Preparation of Formula 205 Referring to Reaction Scheme 2, Steps 3 and 4, a mixture of a compound of Formula 203 and 1 M NaOH in a mixed solvent (e.g., methanol and dioxane) is stirred at room temperature for 5 to 10 hours. The solvents are evaporated and the residue is partitioned (e.g., between dichloromethane, saturated NaCl, and concentrated HCl). The layers are separated and the organic layer dried and concentrated under vacuum to afford the corresponding compound of Formula 204, which crude product is carried forward without further purification. The crude product is redissolved (e.g., in dichloromethane) and treated with a large molar excess of both EDC and diisopropylethylamine. After stirring for 10 to 30 minutes, a large molar excess of an amine of the formula H₂N—$R^5$ (such as benzylamine) is added and the mixture stirred for 12 to 20 hours at room temperature. The mixture is washed, dried and isolated to afford the corresponding crude di-carbamoyl compound of Formula 205, which can be taken forward without further purification.

Prerparation of Formula I or II Referring to Reaction Scheme 2, Step 5, a mixture of a compound of Formula 205 and a large molar excess of K₂CO₃ in a suitable solvent (e.g., ethylene glycol) is stirred at 120° C. for 12 to 20 hours. The solution is cooled to room temperature, diluted with water, and extracted (e.g., with dichloromethane and ethyl acetate). The combined organic layers are washed, isolated and purified to afford the corresponding 1-(acyl)-pyrrolidinyl- or 1-(acyl)-piperidinyl- product of Formula I or II.

Compounds prepared by the above-described process of the invention may be identified by the presence of a detectable amount of Formulae 105 or 205, or a protected precursor of Formula 106. While it is well known that pharmaceuticals must meet pharmacopoeia standards before approval and/or marketing, and that synthetic reagents (such as benzylamine, ethylene glycol or NaOH) and precursors (such as Formulae 105, 106 and 205) should not exceed the limits prescribed by pharmacopoeia standards, final compounds prepared by a process of the present invention may have minor, but detectable, amounts of such materials present, for example at levels in the range of 95% purity with no single impurity greater than 1%. These levels can be detected, e.g., by emission spectroscopy. It is important to monitor the purity of pharmaceutical compounds for the presence of such materials, which presence is additionally disclosed as a method of detecting use of a process of the invention.

Particular Optional Processes and Last Steps

A compound of Formula 205 is cyclized under basic conditions to afford a corresponding, optionally protected 2-[1-(acyl)-pyrrolidinyl]-3H-quinazolin-4-one or 2-[1-(acyl)-piperidinyl]-3-quinazolin-4-one of Formula I.

A protected precursor to Formula I or II (e.g., Formula 106 where $R^{6'}$ is NHBoc) is de-protected with in TFA in a suitable solvent to afford the corresponding de-protected compound of Formula I or II.

A compound of Formula I or II where $R^6$ is hydrogen is contacted with an alkyl or aryl halide, aldehyde or acid chloride in a suitable solvent to afford the corresponding compound of Formula I or II where $R^6$ is other than hydrogen.

A racemic mixture of isomers of a compound of Formula I or II is placed on a chromatography column and separated into (R)— and (S)-enantiomers.

A compound of Formula I or II is contacted with a pharmaceutically acceptable acid to form the corresponding acid addition salt.

A pharmaceutically acceptable acid addition salt of Formula I or II is contacted with a base to form the corresponding free base of Formula I or II.

Particular Compounds

Particular embodiments of the invention include or employ the compounds of Formulae I and II having the following combinations and permutations of substituent groups (indented/sub-grouped, respectively, in increasing order of particularity). These are presented in support of the appended claims as well as combinations and permutations of substituent groups that may, for the sake of brevity, not be specifically claimed but should be appreciated as encompassed by the teachings of the present disclosure. In that regard, the below-described subsets for each substituent (sometimes referenced by paragraph number) are intended to apply to that substituent alone or in combination with one, several, or all of the described subsets for the other substituents.

W, X, Y and Z are independently chosen from —C═ and —N═.
W, X, Y and Z are —C═.
$R^1$, $R^2$, $R^3$ and $R^4$ are independently chosen from hydrogen, halo, lower alkyl, substituted lower alkyl, lower alkoxy, and cyano.
  $R^1$, $R^2$, $R^3$ and $R^4$ are independently hydrogen, chloro, fluoro, methyl, methoxy, cyano or substituted lower alkyl.
  $R^1$, $R^2$, $R^3$ and $R^4$ are independently hydrogen, chloro, fluoro, methyl, methoxy or cyano.
  Where three or four of $R^1$, $R^2$, $R^3$ and $R^4$ are hydrogen.
    $R^1$, $R^2$, $R^3$ and $R^4$ are hydrogen or three of $R^1$, $R^2$, $R^3$ and $R^4$ are hydrogen and the fourth is halo, methoxy, methyl, or cyano.
    Where halo is chloro.
      Where $R^3$ is hydrogen or chloro.
      Where $R^3$ is chloro.
    Where $R^1$, $R^2$, $R^{3'}$ and $R^4$ are hydrogen.
$R^5$ is optionally substituted aralkyl.
  $R^5$ is benzyl or substituted benzyl.
  $R^5$ is benzyl.
T is optionally substituted lower alkylene or is a covalent bond (i.e., absent).
  T is a covalent bond, $C_1$ to $C_4$ alkylene or $C_1$ to $C_4$ alkylene substituted with halo or oxo.
  T is a covalent bond or $C_1$ to $C_4$ alkylene.
  T is a covalent bond.
  Where T is alkylene having a carbon substituted by a heteroatom, the heteroatom is not bound directly to the bicyclic structure.
  T is aminoalkylene or amidoalkylene.
  T is alkylene or alkylene substituted with halo or oxo.
$R^a$, $R^b$, $R^c$, $R^d$, $R^e$, $R^f$, $R^g$ and $R^h$ are independently chosen from hydrogen, lower alkyl (especially methyl), and substituted lower alkyl.
  Where no more than one of $R^a$ to $R^h$ is other than hydrogen.
  Where all of $R^a$ to $R^h$ are hydrogen.
U—V is —N($R^6$)—$CR^eR^f$—$CR^gR^h$—, $CR^eR^f$—N($R^6$)—$CR^gR^h$—, or —$CR^eR^f$—$CR^gR^h$—N($R^6$)—.
  U—V is —N($R^6$)$CR^eR^f$—$CR^gR^h$ or —$CR^eR^f$—N($R^6$)—$CR^gR^h$—.
  Where $R^6$ is optionally substituted aralkyl or optionally substituted acyl.
  Where $R^6$ is optionally substituted acyl.
    Where $R^6$ is p-methyl-benzoyl.
  U—V is —N($R^6$)—$CR^eR$—$CR^gR^h$.
    Where $R^6$ is optionally substituted aralkyl or optionally substituted acyl.
      Where $R^6$ is optionally substituted acyl.
        Where $R^6$ is p-methyl-benzoyl.

Illustrative of the suitable combinations and permutations of particular substituents are the compounds, pharmaceutically acceptable salts and solvates where T is a covalent bond, U—V is —N($R^6$)—$CR^eR^f$—$CR^gR^h$—, and one or more of W, X, Y and Z, $R^1$ to $R^6$, and $R^a$ to $R^h$ is/are as described in paragraphs 089 to 094 above, such as:
  Where $R^1$, $R^2$, $R^3$ and $R^4$ are hydrogen or three of $R^1$, $R^2$, $R^3$ and $R^4$ are hydrogen and the fourth is halo, methoxy, methyl, or cyano.
    Where $R^3$ is chloro.
    Where $R^1$, $R^2$, $R^3$ and $R^4$ are hydrogen.
  Where $R^5$ is optionally substituted benzyl.
    $R^5$ is benzyl.
  Where all but one of $R^a$, $R^b$, $R^c$, $R^d$, $R^e$, $R^f$, $R^g$ and $R^h$ are hydrogen, and the remaining member is chosen from hydrogen, lower alkyl (especially methyl) and substituted lower alkyl.
    All of $R^a$ to $R^h$ are hydrogen.
  Where $R^6$ is optionally substituted acyl.
    $R^6$ is p-methyl-benzoyl.
    Where all but one of $R^a$, $R^b$, $R^c$, $R^d$, $R^e$, $R^f$, $R^g$ and $R^h$ are hydrogen, and the remaining member is chosen from hydrogen, lower alkyl (especially methyl) and substituted lower alkyl.
      All of $R^a$ to $R^h$ are hydrogen.
      Where $R^5$ is optionally substituted benzyl.
        $R^5$ is benzyl.
          Where $R^1$, $R^2$, $R^3$ and $R^4$ are hydrogen or three of $R^1$, $R^2$, $R^3$ and $R^4$ are hydrogen and the fourth is halo, methoxy, methyl, or cyano.

Where $R^3$ is chloro.
   Where $R^1$, $R^2$, $R^3$ and $R^4$ are hydrogen.
Where $R^1$, $R^2$, $R^3$ and $R^4$ are hydrogen or three of $R^1$, $R^2$, $R^3$ and $R^4$ are hydrogen and the fourth is halo, methoxy, methyl, or cyano.
   Where $R^3$ is chloro.
   Where $R^1$, $R^2$, $R^3$ and $R^4$ are hydrogen.
Where $R^1$, $R^2$, $R^3$ and $R^4$ are hydrogen or three of $R^1$, $R^2$, $R^3$ and $R^4$ are hydrogen and the fourth is halo, methoxy, methyl, or cyano.
   Where $R^3$ is chloro.
   Where $R^1$, $R^2$, $R^3$ and $R^4$ are hydrogen.
Where $R^5$ is optionally substituted benzyl.
   $R^5$ is benzyl.
      Where $R^1$, $R^2$, $R^3$ and $R^4$ are hydrogen or three of $R^1$, $R^2$, $R^3$ and $R^4$ are hydrogen and the fourth is halo, methoxy, methyl, or cyano.
      Where $R^3$ is chloro.
      Where $R^1$, $R^2$, $R^3$ and $R^4$ are hydrogen.
   Where $R^1$, $R^2$, $R^3$ and $R^4$ are hydrogen or three of $R^1$, $R^2$, $R^3$ and $R^4$ are hydrogen and the fourth is halo, methoxy, methyl, or cyano.
      Where $R^3$ is chloro.
      Where $R^1$, $R^2$, $R^3$ and $R^4$ are hydrogen.
   Where $R^1$, $R^2$, $R^3$ and $R^4$ are hydrogen or three of $R^1$, $R^2$, $R^3$ and $R^4$ are hydrogen and the fourth is halo, methoxy, methyl, or cyano.
      Where $R^3$ is chloro.
      Where $R^1$, $R^2$, $R^3$ and $R^4$ are hydrogen.
Where $R^5$ is optionally substituted benzyl.
   $R^5$ is benzyl.
      Where $R^1$, $R^2$, $R^3$ and $R^4$ are hydrogen or three of $R^1$, $R^2$, $R^3$ and $R^4$ are hydrogen and the fourth is halo, methoxy, methyl, or cyano.
      Where $R^3$ is chloro.
      Where $R^1$, $R^2$, $R^3$ and $R^4$ are hydrogen.
   Where $R^1$, $R^2$, $R^3$ and $R^4$ are hydrogen or three of $R^1$, $R^2$, $R^3$ and $R^4$ are hydrogen and the fourth is halo, methoxy, methyl, or cyano.
      Where $R^3$ is chloro.
      Where $R^1$, $R^2$, $R^3$ and $R^4$ are hydrogen.
Where all but one of $R^a$, $R^b$, $R^c$, $R^d$, $R^e$, $R^f$, $R^g$ and $R^h$ are hydrogen, and the remaining member is chosen from hydrogen, lower alkyl (especially methyl) and substituted lower alkyl.
All of $R^a$ to $R^h$ are hydrogen.
   Where $R^5$ is optionally substituted benzyl.
      $R^5$ is benzyl.
         Where $R^1$, $R^2$, $R^3$ and $R^4$ are hydrogen or three of $R^1$, $R^2$, $R^3$ and $R^4$ are hydrogen and the fourth is halo, methoxy, methyl, or cyano.
         Where $R^3$ is chloro.
         Where $R^1$, $R^2$, $R^3$ and $R^4$ are hydrogen.
      Where $R^1$, $R^2$, $R^3$ and $R^4$ are hydrogen or three of $R^1$, $R^2$, $R^3$ and $R^4$ are hydrogen and the fourth is halo, methoxy, methyl, or cyano.
         Where $R^3$ is chloro.
         Where $R^1$, $R^2$, $R^3$ and $R^4$ are hydrogen.
      Where $R^1$, $R^2$, $R^3$ and $R^4$ are hydrogen or three of $R^1$, $R^2$, $R^3$ and $R^4$ are hydrogen and the fourth is halo, methoxy, methyl, or cyano.
         Where $R^3$ is chloro.
         Where $R^1$, $R^2$, $R^3$ and $R^4$ are hydrogen.
Where $R^5$ is optionally substituted benzyl.
   $R^5$ is benzyl.
      Where $R^1$, $R^2$, $R^3$ and $R^4$ are hydrogen or three of $R^1$, $R^2$, $R^3$ and $R^4$ are hydrogen and the fourth is halo, methoxy, methyl, or cyano.
      Where $R^3$ is chloro.
      Where $R^1$, $R^2$, $R^3$ and $R^4$ are hydrogen.
   Where $R^1$, $R^2$, $R^3$ and $R^4$ are hydrogen or three of $R^1$, $R^2$, $R^3$ and $R^4$ are hydrogen and the fourth is halo, methoxy, methyl, or cyano.
      Where $R^3$ is chloro.
      Where $R^1$, $R^2$, $R^3$ and $R^4$ are hydrogen.
   Where $R^1$, $R^2$, $R^3$ and $R^4$ are hydrogen or three of $R^1$, $R^2$, $R^3$ and $R^4$ are hydrogen and the fourth is halo, methoxy, methyl, or cyano.
      Where $R^3$ is chloro.
      Where $R^1$, $R^2$, $R^3$ and $R^4$ are hydrogen.
   Where $R^1$, $R^2$, $R^3$ and $R^4$ are hydrogen or three of $R^1$, $R^2$, $R^3$ and $R^4$ are hydrogen and the fourth is halo, methoxy, methyl, or cyano.
      Where $R^3$ is chloro.
      Where $R^1$, $R^2$, $R^3$ and $R^4$ are hydrogen.
Where $R^5$ is optionally substituted benzyl.
   $R^5$ is benzyl.
      Where $R^1$, $R^2$, $R^3$ and $R^4$ are hydrogen or three of $R^1$, $R^2$, $R^3$ and $R^4$ are hydrogen and the fourth is halo, methoxy, methyl, or cyano.
      Where $R^3$ is chloro.
      Where $R^1$, $R^2$, $R^3$ and $R^4$ are hydrogen.
   Where $R^1$, $R^2$, $R^3$ and $R^4$ are hydrogen or three of $R^1$, $R^2$, $R^3$ and $R^4$ are hydrogen and the fourth is halo, methoxy, methyl, or cyano.
      Where $R^3$ is chloro.
      Where $R^1$, $R^2$, $R^3$ and $R^4$ are hydrogen.
Where $R^1$, $R^2$, $R^3$ and $R^4$ are hydrogen or three of $R^1$, $R^2$, $R^3$ and $R^4$ are hydrogen and the fourth is halo, methoxy, methyl, or cyano.
   Where $R^3$ is chloro.
   Where $R^1$, $R^2$, $R^3$ and $R^4$ are hydrogen.

Thus, the compounds where T is a covalent bond and U—V is —N($R^6$)—$CR^eR^f$—$CR^gR^h$, including those where the above-described groupings and sub-groups of substituents are taken individually and/or combined together as illustrated with regard to those compounds where $R^6$ is optionally substituted acyl, are particularly suitable for practice of the present invention.

One group of compounds, pharmaceutically acceptable salts and solvates thereof, compositions including pharmaceutical formulations, and methods of manufacture and use of the present invention are those wherein the compound of Formula I or II is selected from:

3-benzyl-7-chloro-2-[1-(4-methyl-benzyl)-pyrrolidin-2-yl]-3H-quinazolin-4-one;

3-benzyl-7-chloro-2-[1-(4-methyl-benzoyl)-pyrrolidin-2-yl]-3H-quinazolin-4-one;

3-benzyl-7-chloro-2-[1-(4-methyl-benzoyl)-piperidin-2-yl]-3H-quinazolin-4-one;

3-benzyl-7-chloro-2-[1-(4-methyl-benzyl)-piperidin-3-yl]-3H-quinazolin-4-one;

3-benzyl-7-chloro-2-[1-(4-methyl-benzoyl)-piperidin-3-yl]-3H-quinazolin-4-one;

3-benzyl-7-chloro-2-[1-(4-methyl-benzyl)-piperidin-4-yl]-3H-quinazolin-4-one; and 3-benzyl-7-chloro-2-[1-(4-methyl-benzoyl)-piperidin-4-yl]-3H-quinazolin-4-one, especially the (R)-enantiomers thereof.

A particular group of compounds, pharmaceutically acceptable salts and solvates thereof, compositions including pharmaceutical formulations, and methods of manufacture and use of the present invention are those wherein the compound of Formula I or II is selected from:

3-benzyl-7-chloro-2-[1-(4-methyl-benzoylpyrrolidin-2-yl]-3H-quinazolin-4-one;

3-benzyl-7-chloro-2-[1-(4-methyl-benzoylypiperidin-2-yl]-3H-quinazolin-4-one;

3-benzyl-7-chloro-2-[1-(4-methyl-benzoyl)-piperidin-3-yl]-3H-quinazolin-4-one; and 3-benzyl-7-chloro-2-[1-(4methyl-benzoyl)-piperidin-4-yl]-3H-quinazolin-4-one, especially the (R)-enantiomers thereof.

Another particular group of compounds, pharmaceutically acceptable salts and solvates thereof, compositions including pharmaceutical formulations, and methods of manufacture and use of the present invention are those wherein the compound of Formula I or 11 is selected from:

3-benzyl-7-chloro-2-[1-(4-methyl-benzoyl)-piperidin-2-yl]-3H-quinazolin-4-one; and 3-benzyl-7-chloro-2-[1-(4-methyl-benzoylypiperidin-3-yl]-3H-quinazolin-4-one, especially the (R)-enantiomers thereof.

Utility, Testing and Administration

General Utility

The compounds of the invention find use in a variety of applications, including as therapeutic active agents, in the practice of the methods of treatment, in compositions, particularly pharmaceutical formulations and in methods for the manufacture of pharmaceutical formulations, and as intermediates in the synthesis of such therapeutic active agents.

As will be appreciated by those in the art, mitosis can be altered in a variety of ways; that is, one can affect mitosis either by increasing, decreasing or otherwise interfering with the activity of a component in the mitotic pathway. Stated differently, mitosis can be affected (e.g., disrupted) by disturbing equilibrium, either by inhibiting or activating certain mitotic components. Similar approaches can be used to alter meiosis.

The compounds of the invention can be used to inhibit mitotic spindle formation. Such inhibition may take the form of lessening a mitotic kinesin's organization of microtubules into bipolar structures, increasing or decreasing spindle pole separation, and/or inducing mitotic spindle dysfunction. In particular, the compounds of the invention are useful to bind to and/or inhibit the activity of a mitotic kinesin, KSP, especially human KSP, although KSP kinesins from other organisms may also be used. Also included within the definition of the term "KSP" for these purposes are variants and/or fragments of KSP. See, U.S. Pat. No. 6,437,115. While other mitotic kinesins may be used in the present invention, the compounds of the invention have been shown to have specificity for KSP. Contacting a compound of the invention with a KSP kinesin, particularly human KSP kinesin, can lead to diminished KSP-mediated ATP hydrolysis activity and/or diminished KSP-mediated mitotic spindle formation activity. Meiotic spindles can be similarly disrupted.

In another embodiment, the compounds of the invention can be used to modulate one or more other human mitotic kinesins, in addition to inhibiting KSP, including: HSET (see, U.S. Pat. No. 6,361,993); MCAK (see, U.S. Pat. No. 6,331,424); CENP-E (see, PCT Publication No. WO 99/13061); Kif4 (see, U.S. Pat. No. 6,440,684); MKLP1 (see, U.S. Pat. No. 6,448,025); Kif15 (see, U.S. Pat. No. 6,355,466); Kid (see, U.S. Pat. No. 6,387,644); Mpp1, CMKrp, Kinl-3 (see, U.S. Pat. No. 6,461,855); Kip3a (see, PCT Publication No. WO 01/96593); Kip3d (see, U.S. Pat. No. 6,492,151); and RabK6.

Therapeutic uses facilitated by the mitotic kinesin-inhibitory activity of the compounds of the present invention include the treatment of disorders associated with cell proliferation.

Particular disease states that can be treated by the methods, pharmaceutical formulations, and compounds provided herein include, but are not limited to, cancer (further discussed below), autoimmune disease, arthritis, graft rejection, inflammatory bowel disease, proliferation induced after medical procedures, including, but not limited to, surgery, angioplasty, and the like. In one embodiment, the invention includes application to cells or individuals afflicted or impending afflication with any one of these disorders or states.

The compounds, pharmaceutical formulations and methods provided herein are particularly deemed useful for the treatment of cancer including solid tumors such as skin, breast, brain, cervical carcinomas, testicular carcinomas, etc. More particularly, cancers that can be treated include, but are not limited to:

Cardiac: sarcoma (angiosarcoma, fibrosarcoma, rhabdomyosarcoma, liposarcoma), myxoma, rhabdomyoma, fibroma, lipoma and teratoma;

Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma;

Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma);

Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma);

Liver: hepatoma (hepatocellular carcinoma), cholangiocarcinoma, hepatoblastoma, angiosarcoma, hepatocellular adenoma, hemangioma;

Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors;

Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma);

Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma);

Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma];

Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma.

As used herein, treatment of cancer includes treatment of cancerous cells, including cells afflicted by any one of the above-identified conditions.

Another useful aspect of the invention is a kit having a compound, salt or solvate of Formula I or II and a package insert or other labeling including directions treating a cellular proliferative disease by administering an effective amount of the compound, salt or solvate. The compound, salt or solvate of Formula I or II in the kits of the invention is particularly provided as one or more doses for a course of treatment for a cellular proliferative disease, each dose being a pharmaceutical formulation including a pharmaceutically accepted excipient and a compound, salt or solvate of Formula I or II.

Testing

To assay activity, generally, either KSP or a compound according to the invention is non-diffusably bound to an insoluble support having isolated sample receiving areas. The insoluble support can be made of any material to which the compounds can be bound, is readily separated from soluble material, and is otherwise compatible with the overall method of screening. The surface of such supports can be solid or porous and of any convenient shape. Examples of suitable insoluble supports include microliter plates, arrays, membranes and beads. These are typically made of glass, plastic (e.g., polystyrene), polysaccharides, nylon or nitrocellulose, Teflon™, etc. Microtiter plates and arrays are especially convenient because a large number of assays can be carried out simultaneously, using small amounts of reagents and samples. The particular manner of binding of the compound is not crucial so long as it is compatible with the reagents and overall methods of the invention, maintains the activity of the compound and is nondiffusable. Particular methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas can then be blocked through incubation with bovine serum albumin (BSA), casein or other innocuous protein or other moiety.

The compounds of the invention can be used on their own to modulate the activity of a mitotic kinesin, particularly KSP. In this embodiment, a compound of the invention is combined with KSP and the activity of KSP is assayed. Measurable kinesin activities include the ability to affect ATP hydrolysis; microtubule binding; gliding and polymerization/depolymerization (effects on microtubule dynamics); binding to other proteins of the spindle; binding to proteins involved in cell-cycle control; serving as a substrate to other enzymes, such as kinases or proteases; and specific kinesin cellular activities such as spindle pole separation.

Methods of performing motility assays are well known to those of skill in the art. [See e.g., Hall, et al. (1996), Biophys. J., 71: 3467-3476, Turner et al., 1996, AnaL Biochem. 242 (1):20-5; Gittes et al., 1996, Biophys. J. 70(I): 418-29; Shirakawa et al., 1995, J. Exp. BioL 198: 1809-15; Winkelmann et al., 1995, Biophys. J. 68: 2444-53; Winkelmann et al., 1995, Biophys. J. 68: 72S.]

Methods known in the art for determining ATPase hydrolysis activity also can be used.

Solution based assays are particularly suitable (see, U.S. Pat. No. 6,410,254); alternatively, conventional methods are used. For example, $P_i$ release from kinesin can be quantified. In one embodiment, the ATPase hydrolysis activity assay utilizes 0.3 M PCA (perchloric acid) and malachite green reagent (8.27 mM sodium molybdate II, 0.33 mM malachite green oxalate, and 0.8 mM Triton X-1 00). To perform the assay, 10 µL of reaction is quenched in 90 µL of cold 0.3 M PCA. Phosphate standards are used so data can be converted to mM inorganic phosphate released. When all reactions and standards have been quenched in PCA, 100 µL of malachite green reagent is added to the relevant wells in e.g., a microtiter plate. The mixture is developed for 10-15 minutes and the plate is read at an absorbance of 650 nm.

When phosphate standards are used, absorbance readings can be converted to mM $P_i$ and plotted over time. Additionally, ATPase assays known in the art include the luciferase assay.

ATPase activity of kinesin motor domains also can be used to monitor the effects of modulating agents. In one embodiment ATPase assays of kinesin are performed in the absence of microtubules. In another embodiment, the ATPase assays are performed in the presence of microtubules. Different types of modulating agents can be detected in the above assays. In one particular embodiment, the effect of a modulating agent is independent of the concentration of microtubules and ATP. In another embodiment, the effect of the agents on kinesin ATPase can be decreased by increasing the concentrations of ATP, microtubules or both. In yet another embodiment, the effect of the modulating agent is increased by increasing concentrations of ATP, microtubules or both.

Agents that modulate the biochemical activity of KSP in vitro may then be screened in vivo. Methods for testing such agents in vivo include assays of cell cycle distribution, cell viability, or the presence, morphology, activity, distribution or amount of mitotic spindles. Methods for monitoring cell cycle distribution of a cell population, for example, by flow cytometry, are well known to those skilled in the art, as are methods for determining cell viability. See, for example, WO 01/31335, entitled "Methods of Screening for Modulators of Cell Proliferation and Methods of Diagnosing Cell Proliferation States."

In addition to the assays described above, microscopic methods for monitoring spindle formation and malformation are well known to those of skill in the art (see, e.g., Whitehead and Rattner (1998), J. Cell Sci. 111:2551-61; Galgio et al, (1996) J. Cell Biol., 135:399-414).

The compounds of the invention inhibit KSP kinesin. One measure of inhibition, $IC_{50}$, is defined as the concentration of the compound at which the activity of KSP is decreased by fifty percent. Particularly suitable compounds have $IC_{50}$'s of less than about 1 mM, with more particularly suitable compounds having IC$_{50}$'s of less than about 100 μM. IC$_{50}$'s of less than about 10 nM can be attained by certain compounds of the invention, and the pharmaceutically acceptable salts and solvates thereof, it being appreciated that a smaller IC$_{50}$ is generally considered advantageous. Measurement of IC$_{50}$ is done using an ATPase assay.

Another measure of inhibition is K$_i$. For compounds with IC$_{50}$'s less than 1 μM, the K$_i$ or K$_d$ is defined as the dissociation rate constant for the interaction of the test compound with KSP. Particularly suitable compounds have K$_i$'s of less than about 100 μM, more particularly suitable compounds having K$_i$'s of less than about 10 μM. Ki's of less than about 10 nM can be attained by certain compounds of the invention, and the pharmaceutically acceptable salts and solvates thereof, it being appreciated that a smaller K$_i$ is generally considered advantageous. The K$_i$ for a compound is determined from the IC$_{50}$ based on three assumptions. First, only one compound molecule binds to the enzyme and there is no cooperativity. Second, the concentrations of active enzyme and the compound tested are known (i.e., there are no significant amounts of impurities or inactive forms in the preparations). Third, the enzymatic rate of the enzyme-inhibitor complex is zero. The rate (i.e., compound concentration) data are fitted to the equation:

$$V = V_{max}E_0\left[1 - \frac{(E_0 + I_0 + Kd) - \sqrt{(E_0 + I_0 + Kd)^2 - 4E_0I_0}}{2E_0}\right]$$

Where V is the observed rate, V$_{max}$ is the rate of the free enzyme, I$_0$ is the inhibitor concentration, E$_0$ is the enzyme concentration, and K$_d$ is the dissociation constant of the enzyme-inhibitor complex.

Another measure of inhibition is GI$_{50}$, defined as the concentration of the compound that results in a decrease in the rate of cell growth by fifty percent. Anti-proliferative compounds that have been successfully applied in the clinic to treatment of cancer (cancer chemotherapeutics) have GI$_{50}$'s that vary greatly. For example, in A549 cells, paclitaxel GI$_{50}$ is 4 nM, doxorubicin is 63 nM, 5-fluorouracil is 1 μM, and hydroxyurea is 500 μM (data provided by National Cancer Institute, Developmental Therapeutic Program, http://dtp.nci.nih.gov/). Therefore, compounds that inhibit cellular proliferation at virtually any concentration may be useful. Particularly suitable compounds have GI$_{50}$'s of less than about 1 mM, with more particularly suitable compounds having a GI$_{50}$ of less than about 10 μM. GI$_{50}$'s of less than about 10 nM can be attained by certain compounds of the invention, and the pharmaceutically acceptable salts and solvates thereof, it being appreciated that a smaller GI$_{50}$ is generally considered advantageous. Measurement of GI$_{50}$ is done using a cell proliferation assay.

Testing for growth inhibition using cell lines (such as MCF-7/ADR-RES and HCT1 5) that express P-glycoprotein (also known as Multi-drug Resistance, or MDR$^+$), which conveys resistance to other chemotherapeutic drugs, such as pacilitaxel, can identify anti-mitotic agents that inhibit cell proliferation and are not subject to resistance by overexpression of MDR$^+$ by drug-resistant tumor lines.

In vitro potency of small molecule inhibitors is determined by assaying human ovarian cancer cells (SKOV3) for viability following a 72-hour exposure to a 9-point dilution series of compound. Cell viability is determined by measuring the absorbance of formazon, a product formed by the bioreduction of MTS/PMS, a commercially available reagent. Each point on the dose-response curve is calculated as a percent of untreated control cells at 72 hours minus background absorption (complete cell kill).

To employ the compounds of the invention in a method of screening for compounds that bind to KSP kinesin, the KSP is bound to a support, and a compound or composition of the invention is added to the assay. Alternatively, a composition of a compound of the invention bound to a solid support can be made, and KSP added to the assay. Classes of compounds among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the mitotic agent to KSP may be done in a number of ways. In a particular embodiment, the compound of the invention is labeled, for example, with a fluorescent or radioactive moiety and binding determined directly. For example, this may be done by attaching all or a portion of KSP to a solid support, adding a labeled compound (for example a compound of the invention in which at least one atom has been replaced by a detectable isotope), washing off excess reagent, and determining whether the amount of the label is that present on the solid support. Various blocking and washing steps may be utilized as is known in the art.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the kinesin proteins may be labeled at tyrosine positions using $^{125}$I, or with fluorophores. Alternatively, more than one component may be labeled with different labels; using $^{125}$I for the proteins, for example, and a fluorophor for the anti-mitotic agents.

The compounds of the invention may also be used as competitors to screen for additional drug candidates. "Candidate agent" or "drug candidate" or grammatical equivalents as used herein describe any molecule, e.g., protein, oligopeptide, small organic molecule, polysaccharide, polynucleotide, etc., to be tested for bioactivity. They may be capable of directly or indirectly altering the cellular proliferation phenotype or the expression of a cellular proliferation sequence, including both nucleic acid sequences and protein sequences. In other cases, alteration of cellular proliferation protein binding and/or activity is screened. Screens of this sort may be performed either in the presence or absence of microtubules. In the case where protein binding or activity is screened, particular embodiments exclude molecules already known to bind to that protein, for example, polymer structures such as microtubules, and energy sources such as ATP. Particular embodiments of assays herein include candidate agents that do not bind the cellular proliferation protein in its endogenous native state termed herein as "exogenous" agents. In another particular embodiment, exogenous agents further exclude antibodies to KSP.

Candidate agents can encompass numerous chemical classes, though typically they are organic molecules, particularly small organic compounds having a molecular weight of more than 100 and less than about 2,500 daltons. Candidate agents comprise functional groups necessary for structural interaction with proteins, particularly hydrogen bonding and lipophilic binding, and typically include at least an amine, carbonyl, hydroxyl, ether, or carboxyl group, especially at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

Competitive screening assays can be done by combining KSP and a drug candidate in a first sample. A second sample may be made combining a compound of the invention, KSP and a drug candidate. This may be performed in either the presence or absence of microtubules. The binding of the drug candidate is determined for both samples, and a change or difference in binding between the two samples indicates the presence of an agent capable of binding to KSP and potentially modulating its activity. That is, if the binding of the drug candidate is different in the second sample relative to the first sample, the drug candidate is capable of binding to KSP.

In a particularly suitable embodiment, the binding of the candidate agent is determined through the use of competitive binding assays. In this embodiment, the competitor is a binding moiety known to bind to KSP, such as an antibody, peptide, binding partner, ligand, etc. Under certain circumstances, there may be competitive binding as between the candidate agent and the binding moiety, with the binding moiety displacing the candidate agent.

In one embodiment, the candidate agent is labeled. Either the candidate agent, or the competitor, or both, is added first to KSP for a time sufficient to allow binding, if present. Incubations can be performed at any temperature that facilitates optimal activity, typically between 4 and 40° C. Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In a particularly suitable embodiment, the competitor is added first, followed by the candidate agent. Displacement of the competitor is an indication the candidate agent is binding to KSP and thus is capable of binding to, and potentially modulating, the activity of KSP. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to KSP with a higher affinity. Thus, if the candidate agent is labeled, the presence of the label on the support, coupled with a lack of competitor binding, may indicate the candidate agent is capable of binding to KSP.

It may be of value to identify the binding site of KSP. This can be done in a variety of ways. In one embodiment, once KSP has been identified as binding to the compound, KSP is fragmented or modified and the assays repeated to identify the necessary components for binding.

Modulation is tested by screening for candidate agents capable of modulating the activity of KSP comprising the steps of combining a candidate agent with KSP, as above, and determining an alteration in the biological activity of KSP. Thus, in this embodiment, the candidate agent should both bind to KSP (although this may not be necessary), and alter its biological or biochemical activity as defined herein. The methods include both in vitro screening methods and in vivo screening of cells for alterations in cell cycle distribution, cell viability, or for the presence, morpohology, activity, distribution, or amount of mitotic spindles, as are generally outlined above.

Alternatively, differential screening may be used to identify drug candidates that bind to the native KSP, but cannot bind to modified KSP.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents can be included in the screening assays. These include reagents like salts, neutral proteins, e.g., albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Formulation and Administration

The compounds, pharmaceutically acceptable salts and solvates of Formula I and II are administered at a therapeutically effective dosage, e.g., a dosage sufficient to provide treatment for the disease states previously described. Human dosage levels are typically determined by escalating dose ranging studies conducted in accordance with current Good Clinical Practice, FDA and local guidelines. The amount of active compound administered will, of course, be dependent on the subject and disease state being treated, the severity of the affliction, the manner and schedule of administration and the judgment of the prescribing physician.

The administration of the compounds and pharmaceutical formulations of the present invention can be done in a variety of ways, including, but not limited to, orally, subcutaneously, intravenously, intranasally, transdermally, intraperitoneally, intramuscularly, intrapulmonary, vaginally, rectally, or intraoculariy. In some instances, for example, in the treatment of wounds and inflammation, the compound or composition may be directly applied as a solution or spray.

Pharmaceutical formulations include a compound of Formula I or II or a pharmaceutically acceptable salt or solvate thereof, and one or more pharmaceutically acceptable excipients. As is known in the art, pharmaceutical excipients are secondary ingredients that function to enable or enhance the delivery of a drug or medicine in a variety of dosage forms (e.g.: oral forms such as tablets, capsules, and liquids; topical forms such as dermal, opthalmic, and otic forms; suppositories; injectables; respiratory forms and the like). Pharmaceutical excipients include inert or inactive ingredients, synergists or chemicals that substantively contribute to the medicinal effects of the active ingredient. For example, pharmaceutical excipients may function to improve flow characteristics, product uniformity, stability, taste, or appearance, to ease handling and administration of dose, for convenience of use, or to control bioavailability. While pharmaceutical excipients are commonly described as being inert or inactive, it is appreciated in the art that there is a relationship between the properties of the pharmaceutical excipients and the dosage forms containing them.

Pharmaceutical excipients suitable for use as carriers or diluents are well known in the art, and may be used in a variety of formulations. See, e.g., Remington's Pharmaceutical Sciences, 18th Edition, A. R. Gennaro, Editor, Mack Publishing Company (1990); Remington: The Science and Practice of Pharmacy, 20th Edition, A. R. Gennaro, Editor, Lippincott Williams & Wilkins (2000); Handbook of Pharmaceutical Excipients, 3rd Edition, A. H. Kibbe, Editor, American Pharmaceutical Association, and Pharmaceutical Press (2000); and Handbook of Pharmaceutical Additives, compiled by Michael and Irene Ash, Gower (1995). The concentration of a therapelitically active agent in a formulation can vary widely, from about 0.1 to 99.9 wt. %, depending on the nature of the formulation.

Oral solid dosage forms such as tablets will typically comprise one or more pharmaceutical excipients, which may for example help impart satisfactory processing and compression characteristics, or provide additional desirable physical characteristics to the tablet. Such pharmaceutical excipients may be selected from diluents, binders, glidants, lubricants, disintegrants, colorants, flavorants, sweetening agents, polymers, waxes or other solubility-modulating materials.

Dosage forms for parenteral administration will generally comprise fluids, particularly intravenous fluids, i.e., sterile solutions of simple chemicals such as sugars, amino acids or electrolytes, which can be easily carried by the circulatory system and assimilated. Such fluids are typically prepared with water for injection USP. Fluids used commonly for intravenous (IV) use are disclosed in Remington, The Science and Practice of Pharmacy [full citation previously provided], and include:

- alcohol, e.g., 5% alcohol (e.g., in dextrose and water ("D/W") or D/W in normal saline solution ("NSS"), including in 5% dextrose and water ("D5/W"), or D5/W in NSS);
- synthetic amino acid such as Aminosyn, FreAmine, Travasol, e.g., 3.5 or 7; 8.5; 3.5, 5.5 or 8.5 % respectively;
- ammonium chloride e.g., 2.14%;
- dextran 40, in NSS e.g., 10% or in D5/W e.g., 10%;
- dextran 70, in NSS e.g., 6% or in D5/W e.g., 6%;
- dextrose (glucose, D5/W) e.g., 2.5-50%;
- dextrose and sodium chloride e.g., 5-20% dextrose and 0.22-0.9% NaCl;
- lactated Ringer's (Hartmann's) e.g., NaCl 0.6%, KCl 0.03%, $CaCl_2$ 0.02%;
- lactate 0.3%;
- mannitol e.g., 5%, optionally in combination with dextrose e.g., 10% or NaCl e.g., 15 or 20%;
- multiple electrolyte solutions with varying combinations of electrolytes, dextrose, fructose, invert sugar Ringer's e.g., NaCl 0.86%, KCl 0.03%, $CaCl_2$ 0.033%;
- sodium bicarbonate e.g., 5%;
- sodium chloride e.g., 0.45, 0.9, 3, or 5%;
- sodium lactate e.g., ⅙ M; and
- sterile water for injection The pH of such IV fluids may vary, and will typically be from 3.5 to 8 as known in the art.

The compounds, pharmaceutically acceptable salts and solvates of the invention can be administered alone or in combination with other treatments, i.e., radiation, or other therapeutic agents, such as the taxane class of agents that appear to act on microtubule formation or the camptothecin class of topoisomerase I inhibitors. When so-used, other therapeutic agents can be administered before, concurrently (whether in separate dosage forms or in a combined dosage form), or after administration of an active agent of the present invention.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes.

EXAMPLES

Example 1

3-Benzyl-7-chloro-1-pyrrolidine-2-yl-2,3-dihydro-1H-quinazoline-4-one

1A. Formula 103 where T is a covalent bond: W, X, Y and Z are —C═: U'—V' is —N($R^{6'}$)—C$R^e R^f$—; $R^1$, $R^2$, $R^4$, and $R^a$ to $R^f$ are H: $R^3$ is chloro; and $R^{6'}$ is Boc A solution of pyrrolidine-1,2-dicarboxylic acid 1-tert-butyl ester (6.0 g, 28 mmol), 2-amino-4-chloro-benzoic acid methyl ester (4.6 g, 25 mmol), PyBroP (14.4 g, 31 mmol), diisopropylethylamine (6 mL) in pyridine (60 mL) was stirred overnight at room temperature, after which HPLC/MS showed complete conversion of starting material. The solvents were removed under vacuum and the residue partitioned between ethyl acetate (100 mL) and water (50 mL). The organic layer was washed with 1M HCl (50 mL) and saturated $NaHCO_3$ (50 mL), dried over $MgSO_4$, filtered, and concentrated under vacuum. Silica gel chromatography using 30% ethyl acetate/hexanes as eluent gave 9.3 g (87% yield) of the desired product of Formula 103, 2-(5-chloro-2-methoxycarbonyl-phenylcarbamoyl)-pyrrolidine-1-carboxylic acid tert-butyl ester, as a yellow foam. LRMS (MH+) m/z 383.

1B. Formula 104 where T is a covalent bond; W, X, Y and Z are —C═; U'—V' is —N($R^{6'}$)—C$R^e R^f$—; $R^1$, $R^2$, $R^4$, and $R^a$ to $R^f$ are H; $R^3$ is chloro; and $R^{6'}$ is Boc: A solution of the pure compound of Formula 103 (9.3 g, 24 mmol) dissolved in 125 mL of ethanol was treated with NaOH solution (3.1 g in 16 mL of $H_2O$). The mixture was stirred at room temperature overnight and then concentrated under vacuum. The residue was treated with a solution of saturated NaCl (200 mL) and concentrated phosphoric acid (5 mL) for a few minutes and then extracted with dichloromethane (2×200 mL). The organic fractions were combined, dried over MgSO$_4$, filtered and concentrated give 8.7 g (97% yield) of the clean desired product of Formula 104, 2-(5-chloro-2-carboxy-phenylcarbamoyl)-pyrrolidine-1-carboxylic acid tert-butyl ester, as an orange foam. LRMS (M) m/z 368.

1C. Formula 105 where T is a covalent bond; W, X, Y and Z are —C═; U'—V' is —N(R$^6$)—CR$^e$R$^f$—; R$^1$, R$^2$, R$^4$, and R$^a$ to R$^f$ are H; R$^3$ is chloro; R$^5$ is benzyl, and R$^{6'}$ is Boc:

To a solution of the compound of Formula 104 (8.7 9, 24 mmol) in dichloromethane (250 mL) was added EDC (14.85 g, 77 mmol), and diisopropylethylamine (14.1 mL, 81 mmol). After stirring at room temperature for 1.5 hours, benzylamine (8.4 mL, 77 mmol) was added and the reaction stirred for an additional 48 hours. The mixture was washed with water (2×50 mL), 10% phosphoric acid (2×50 mL), and saturated NaHCO$_3$ (50 mL). The organic phase was dried over MgSO$_4$, filtered and concentrated under vacuum to give a mixture of 9.4 g (88% yield) of the desired product of Formula 105, 2-(2-benzylcarbamoyl-5-chloro-phenylcarbamoyl)-pyrrolidine-1-carboxylic acid tert-butyl ester, as a light yellow foam, together with a small amount of 2-(3-benzyl-7-chloro-4-oxo-3,4-dihydro-2Hquinzoline-1-yl)-pyrrolidine-1-carboxylic acid tert-butyl ester (Formula 106), which was taken on without further purification. LRMS (MH$^+$) m/z 458.

1D. Formula 106 where T is a covalent bond; W, X, Y and Z are —C═; U'—V' is —N(R$^6$)—CR$^e$R$^f$—; R$^1$, R$^2$, R$^4$, and R$^a$ to R$^f$ are H; R$^3$ is chloro; R$^5$ is benzyl, and R$^{6'}$ is Boc:

The mixture of Formulae 105 and 106 (5.4 g, 12 mmol) was stirred in ethylene glycol (32 mL) with K$_2$CO$_3$ (27 g) at 120° C. overnight, after which the solution was allowed to cool to room temperature and was extracted with dichloromethane (3×200 mL). The organic fractions were combined, dried over MgSO$_4$, filtered and concentrated under vacuum. The resulting residue was purified by silica gel chromatography using 20% ethyl acetate/hexanes as eluent to give 1.4 g (27% yield) of the pure desired product of Formula 106, 2-(3-benzyl-7-chloro-4-oxo-3,4-dihydro-2Hquinzoline-1-yl)-pyrrolidine-1-carboxylic acid tert-butyl ester. LRMS (MH$^+$) m/z 439.

1E. Formula I where U—V is —N(R$^6$)—CR$^e$R$^f$—; R$^1$, R$^2$, R$^4$, R$^6$ and R$^a$ to R$^f$ are H; R$^3$ is chloro; and R$^5$ is benzyl: The pure compound of Formula 106 (446 mg, 1.0 mmol) was treated with 20 mL of a 1:1 mixture of TFA/dichloromethane for 1 hour at room temperature. The solution was concentrated under vacuum and partitioned between dichloromethane (20 mL) and saturated NaHCO$_3$ (10 mL). The aqueous layer was extracted with dichloromethane (10 mL) and the combined organic layers were dried over K$_2$CO$_3$, filtered and concentrated to give 344 mg (100% yield) of the desired product of Formula I, 3-benzyl-7-chloro-1-pyrrolidine-2-yl-2,3-dihydro-1H-quinazoline-4-one, which was taken on without further purification. LRMS (MH$^+$) m/z 340.

Example 2

3-Benzyl-7-chloro-2-[1-(4-methyl-benzoyl)-pyrrolidin-2-yl]-3H-quinazolin-4-one

Formula I where U—V is —N(R$^6$)—CR$^e$R$^f$—; R$^1$, R$^2$, R$^4$, and R$^a$ to R$^f$ are H; R$^3$ is chloro; R$^5$ is benzyl: and R$^6$ is p-methyl-benzoyl: To a solution of crude 3-benzyl-7-chloro-1-(pyrrolidine-2-carbonyl)-2,3-dihydro-1H-quinazoline-4-one (250 mg, 0.73 mmol) in dichloromethane (4.5 mL) was added p-toluoyl chloride (0.29 mL, 2.2 mmol) and diisopropylethylamine (0.77 mL, 4.4 mmol). The mixture was stirred for 1 hour and then partitioned between saturated NaHCO$_3$ (10 mL) and ethyl acetate (20 mL). The organic phase was washed with saturated NaHCO$_3$ (3×4 mL) and saturated NaCl (2×4 mL), dried over Na$_2$SO$_4$, filtered and concentrated under vacuum. The crude residue was purified by preparative reverse phase C18 HPLC (10-98% acetonitrile/water) to give 223 mg (66% yield) of the pure desired product of Formula I, 3-benzyl-7-chloro-2-[1-(4-methyl-benzoyl)-pyrrolidin-2-yl]-3H-quinazolin-4-one. LRMS (MH$^+$) m/z 459.

Example 3

3-Benzyl-7-chloro-2-[1-(4-methyl-benzyl)-pyrrolidin-2-yl]-3H-quinazolin-4-one

Formula I where U—V is —N(R$^6$)—CR$^e$R$^f$—; R$^1$, R$^2$, R$^4$, and R$^a$ to R$^f$ are H; R$^3$ is chloro; R$^5$ is benzyl: and R$^6$ is p-methyl-benzyl: Crude 3-benzyl-7-chloro-1-(pyrrolidine-2-carbonyl)-2,3-dihydro-1H-quinazoline-4-one (170 mg, 0.50 mmol) dissolved in dichloromethane (5 mL) was treated with p-tolualdehyde (80 μL, 0.7 mmol) and NaHB(OAc)$_3$ (350 mg, 1.65 mmol), and the mixture was stirred for 40 minutes at room temperature. The reaction was quenched with saturated NaHCO$_3$ (2.2 mL) and the aqueous phase extracted with dichloromethane (25 mL). The organic layers were combined and dried over Na$_2$SO$_3$, filtered and concentrated under vacuum. The crude residue was purified by silica gel chromatography using a stepwise gradient of 20% ethyl acetate/hexanes to 50% methanol/ethyl acetate as eluent to give 52.5 mg (24% yield) of desired product of Formula I, 3-benzyl-7-chloro-2-[1-(4-methyl-benzyl)-pyrrolidin-2-yl]-3Hquinazolin4-one. LRMS (MH$^+$) m/z 445.

Example 4

Other Compounds of Formulae I and II

4A. Formula I where U—V is —CR$^e$R$^f$—CR$^g$R$^h$—N(R$^6$)—; R$^1$, R$^2$, R$^4$, R$^b$ and R$^c$ to R$^h$ are H; R$^3$ is chloro; R$^5$ is methyl; and R$^a$ is phenethyl; and R$^6$ is p-methyl-benzoyl By following the procedure described in Example 1 and substituting pyrrolidine-1,2-dicarboxylic acid 1-tert-butyl ester with 3-phenethyl-piperidine-1,4-dicarboxylic acid tert-butyl ester (in Example 1A), and substituting benzylamine with methylamine (in Example 1C) there is obtained: 7-chloro-2-[3-phenethyl-piperidin-4-yl]-3-methyl-3H-quinazolin-4-one.

4B. Formula I where U—V is —CR$^e$R—CR$^g$R$^h$—N(R$^6$)—; R$^1$, R$^2$, R$^4$, R$^b$ and R$^c$ to R$^h$ are H; R$^3$ is chloro; R$^5$ is methyl; and R$^a$ is phenethyl; and R$^6$ is p-methyl-benzoyl: By following the procedure described in Example 2 and substituting 3-benzyl-7-chloro-1-(pyrrolidine-2-carbonyl)-2,3-dihydro-1H-quinazoline-4-one with 7-chloro-2-[3-phenethyl-piperidin-4-yl]-3-methyl-3H-quinazolin-4-one, there is obtained: 7-chloro-2-[1-(4-methyl-benzoyl)-3-phenethyl-piperidin-4-yl]-3-methyl-3H-quinazolin-4-one.

4C. Formula I where U—V is —CR$^e$R$^f$—CR$^g$R$^h$—N(R$^6$)—; R$^1$, R$^4$, R$^b$ and R$^c$ to R$^h$ are H; R$^2$ and R$^3$ are methoxy; R$^5$ is methyl; and R$^a$ is phenethyl; and R$^6$ is benzyl: By following the procedure described in Example 3, substituting 3-benzyl-7-chloro-1-(pyrrolidine-2-carbonyl)-2,3-dihydro-1H-quinazoline-4-one with 6,7-dimethoxy-2-[3-phenethyl-piperidin-4-yl]-3-methyl-3H-quinazolin-4-one, and substituting p-tolualdehyde with benzaldehyde, there is obtained 6,7-dimethoxy-2-[1-benzyl-3-phenethyl-piperidin4-yl]-3-methyl-3H-quinazolin-4-one.

4D. Compounds of Formula II Varying T By following the procedure described in Example 1 and substituting pyrrolidine-1,2-dicarboxylic acid 1-tert-butyl ester with the following:

2-carboxymethyl-pyrrolidine-1-carboxylic acid tert-butyl ester;
2-(2-carboxy-acetyl)-pyrrolidine-1-carboxylic acid tert-butyl ester; and
2-(2-carboxy-ethyl)-piperidine-1-carboxylic acid tert-butyl ester, there are obtained the following respective compounds:
3-benzyl-7-chloro-2-pyrrolidine-2-ylmethyl-3H-quinazoline-4-one;
3-benzyl-7-chloro-2-(2-oxo-2-pyrrolidine-2-yl-ethyl)-3H-quinazoline-4-one; and
3-benzyl-7-chloro-2-piperidine-2-ylethyl-3H-quinazoline-4-one.

4E. Compounds of Formula II Varying W, X, Y and Z By following the procedure described in Example 1 and substituting 2-amino-4-chloro-benzoic acid methyl ester with the following:
4-amino-6-chloro-nicotinic acid methyl ester;
3-amino-pyrazine-2-carboxylic acid;
3-amino-1,4-dihydro-pyridine-2-carboxylic acid;
2-amino-cyclopent-1-enecarboxylic acid;
4-amino-2,5-dihydro-furan-3-carboxylic acid; and
3-amino-1H-pyrrole-2-carboxylic acid, there are obtained the following respective compounds:
3-benzyl-7-chloro-1-pyrrolidine-2-yl-2,3-dihydro-1H-pyrido[4,3-d]pyrimidin-4-one;
3-benzyl-1-pyrrolidin-2-yl-1H-pteridin-4-one;
3-benzyl-1-pyrrolidin-2-yl-2,3,5,6,7,8-hexahydro-1H-pyrido[3,2-d]pyrimidin-4-one;
3-benzyl-1-pyrrolidin-2-yl-1,2,3,5,6,7-hexahydro-cyclopentapyrimidin-4-one;
3-benzyl-1-pyrrolidin-2-yl-2,3,5,7-tetrahydro-1H-furo[3,4-d]pyrimidin-4-one; and
3-benzyl-1-pyrrolidin-2-yl-1,2,3,5tetrahydro-pyrrolo[3,2-d]pyrimidin-4-one.

Example 5

3-Benzyl-7-chloro-2-[1-(4-methyl-benzoyl)-piperidin-2-yl]-3H-quinazolin-4-one

5A. Formula 202 where T is a covalent bond; U—V is —N($R^6$)—$CR^eR^f$—$CR^gR^h$—; $R^a$ to $R^h$ are H; $R^3$ is chloro; and $R^6$ is p-methyl-benzoyl: To a solution of piperidine-2-carboxylic acid (3.5 g, 15 mmol) in 2M NaOH (70 mL) at 0° C., was added p-toluoyl chloride (2.2 mL, 17 mmol) in 10 equal portions over 1 hour. The mixture was then stirred an additional 1 hour at room temperature. The reaction was cooled to 0° C. and partitioned between 1N HCl and dichloromethane. The organic layer was dried over MgSO$_4$, filtered and concentrated under vacuum to give 4.7 g of oil. 2.0 g of this material was recrystallized from 95% ethanol (2.5 mL) to give 0.86 g of the desired pure crystalline product of Formula 202, 1-(4-methyl-benzoyl)-piperidine-2-carboxylic acid. LRMS (MH$^+$) m/z 248.

5B. Forrmula 203 where T is a covalent bond; W, X, Y and Z are —C=; U—V is —N($R^6$)—$CR^eR^f$—$CR^gR^h$—; $R^1$, $R^2$, $R^4$ and $R^a$ to $R^h$ are H; $R^3$ is chloro; and $R^6$ is p-methyl-benzoyl:

In an ice bath at −15° C., pure compound of Formula 202 (7.2 g, 29 mmol) was combined with 2-amino-4-chloro-benzoic acid methyl ester (4.5 g, 24 mmol), PyBroP (2.3 g, 4.9 mmol) and diisopropylethylamine (0.95 mL, 5.4 mmol) in DMF (30 mL). The resulting mixture was stirred overnight, allowing the temperature to rise to room temperature with the bath. The solution was concentrated under vacuum and the residue partitioned between ethyl acetate (200 mL) and water (200 mL). The organic layer was washed with water (3×100 mL) and concentrated under vacuum. The resulting residue was purified by silica gel chromatography using 40% ethyl acetate/hexanes as eluent to give 2.66 g (21% yield) of the desired product of Formula 203, 4-chloro-2-{[1-(4-methyl-benzoyl)-piperidine-2-carbonyl]amino}-benzoic acid methyl ester, as a crystalline solid. LRMS (MH$^+$) m/z 472.

5C. Formula 205 where T is a covalent bond; W, X, Y and Z are —C=; U—V is —N($R^6$)—$CR^eR^f$—$CR^gR^h$—; $R^1$, $R^2$, $R^4$ and $R^a$ to $R^h$ are H; $R^{and R6}$ is p-methyl-benzoyl: A mixture of the compound of Formula 203 (2.66 g, 6.7 mmol), 1M NaOH (27 mL), methanol (54 mL), and dioxane (36 mL) was stirred at room temperature for 7 hours. The solvents were evaporated and the residue portioned between dichloromethane (75 mL), saturated NaCl (50 mL), and concentrated HCl (3 mL). The layers were separated and the organic layer dried over MgSO$_4$ and concentrated under vacuum to give the corresponding compound of Formula 204, 4-chloro-2-[1-(4-methyl-benzoyl)-piperidine-2-carbonyl]amino}-benzoic acid, which was carried forward without further purification. This crude product was redissolved in dichloromethane and treated with EDC (3.84 g, 20 mmol), and diisopropylethylamine (3.50 mL, 20 mmol). After stirring 20 minutes, benzylamine (2.20 mL, 20 mmol) was added and the mixture stirred overnight at room temperature. The mixture was washed with water (2×50 mL) and 1M HCl, dried over MgSO$_4$, filtered and concentrated under vacuum to give 1.5 g (47% yield) of the desired product of Formula 205, 1-(4-methyl-benzoyl)-piperidine-2-carboxylic acid (2-benzylcarbamoyl-5-chloro-phenyl-amide, a crude product that was found to be 80% pure by reverse phase HPLC. The product was taken on without further purification. LRMS (MH$^+$) m/z 491.

5D. Formula I where U—V is —N($R^6$)—$CR^eR^f$—$CR^gR^h$—; $R^1$, $R^2$, $R^4$ and $R^a$ to $R^h$ are H; $R^3$ is chloro; $R^5$ is benzyl; and $R^6$ is p-methyl-benzoyl: A mixture of the crude product of Formula 205 (170 mg, 0.35 mmol) and K$_2$CO$_3$ (0.8 g, 5.8 mmol) in ethylene glycol (4 mL) was stirred at 120° C. overnight. After cooling to room temperature, the solution was diluted with water (30 mL), and extracted with dichloromethane (30 mL) and ethyl acetate (30 mL). The organic layers were combined and washed with water (2×5 mL) and saturated NaCl (5 mL), dried over Na$_2$SO$_4$, filtered and concentrated under vacuum to give a turbid yellow oil. The crude material was purified by reverse phase C18 HPLC (10-98% acetonitrile/water) to give 19 mg (12% yield) of the desired product of Formula I, 3-benzyl-7-chloro-2-[1-(4-methyl-benzoyl)-piperidin-2-yl]-3H-quinazolin-4-one. LRMS (MH$^+$) m/z 473.

Example 6

Other Compounds of Formulae I and II

6A. Formula I Varving $R^6$: By following the procedure described in Example 5 and substituting p-toluoyl chloride with the following:
benzyl chloride;
benzoyl chloride; and
p-tolyl chloride, there are obtained the following respective compounds:
3-benzyl-7-chloro-2-(1-benzyl-piperidin-2-yl)-3H-quinazolin-4-one;
3-benzyl-7-chloro-2-(1-benzoyl-piperidin-2-yl)-3H-quinazolin-4-one; and
3-benzyl-7-chloro-2-[1-(4-methyl-benzyl)-piperidin-2-yl]-3H-quinazolin-4-one.

6B. Compounds of Formula II Varving T By following the procedure described in Example 5 and substituting piperidine-1,2-dicarboxylic acid with the following:
2-carboxymethyl-pyrrolidine-1-carboxylic acid;
2-(2-carboxy-acetyl)-pyrrolidine-1-carboxylic acid; and
2-(2-carboxy-ethyl)-piperidine-1-carboxylic acid, there are obtained the following respective compounds:
3-benzyl-7-chloro-2-[1-(4-methyl-benzoyl)-pyrrolidine-2-ylmethyl]-3H-quinazoline-4-one;
3-benzyl-7-chloro-2-{2-[1-(4-methyl-benzoyl)-pyrrolidine-2-yl]-2-oxo-ethyl}-3H-quinazoline-4-one; and
3-benzyl-7-chloro-2-[1-(4-methyl-benzoyl)-piperidine-2-yl]-ethyl]-3H-quinazoline-4-one.

6C. Compounds of Formula II Varying W, X, Y and Z By following the procedure described in Example 5 and substituting 2-amino-4-chloro-benzoic acid methyl ester with the following:
4-amino-6-chloro-nicotinic acid methyl ester;
3-aminopyrazine-2-carboxylic acid;
3-amino-1,4-dihydro-pyridine-2-carboxylic acid;
2-amino-cyclopent-1-enecarboxylic acid;
4-amino-2,5-dihydro-furan-3-carboxylic acid; and
3-amino-1H-pyrrole-2-carboxylic acid, there are obtained the following respective compounds:
3-benzyl-7-chloro-1-(4-methyl-benzoyl)pyrrolidine-2-yl-2,3-dihydro-1H-pyrido[4,3-d]pyrimidin-4-one;
3-benzyl-1-(4-methyl-benzoyl)-pyrrolidin-2-yl-1H-pteridin-4-one;
3-benzyl-1-(4-methyl-benzoyl)-pyrrolidin-2-yl-2,3,5,6,7,8-hexahydro-1H-pyrido[3,2-d]pyrimidin-4-one;
3-benzyl-1-(4-methyl-benzoyl)-pyrrolidin-2-yl-1,2,3,5,6,7-hexahydro-cyclopentapyrimidin-4-one;
3-benzyl-1-(4-methyl-benzoyl)-pyrrolidin-2-yl-2,3,5,7-tetrahydro-1H-furo[3,4-d]pyrimidin-4-one; and
3-benzyl-1-(4-methyl-benzoyl)-pyrrolidin-2-yl-1,2,3,5-tetrahydro-pyrrolo[3,2-d]pyrimidin-4-one.

Example 7

Induction of Mitotic Arrest in Cell Populations Treated with a KSP Inhibitor

FACS analysis to determine cell cycle stage by measuring DNA content is performed as follows. Skov-3 cells (human ovarian cancer) are split 1:10 for plating in 10cm dishes and grown to subconfluence with RPMI 1640 medium containing 5% fetal bovine serum (FBS). The cells are then treated with either 10 nM paclitaxel, 400 nM test compound, 200 nM test compound, or 0.25% DMSO (vehicle for compounds) for 24 hours. A well known anti-mitotic agent, such as placitaxel, is used as a positive cotnrol. Cells are then rinsed off the plates with PBS containing 5mM EDTA, pelleted, washed once in PBS containing 1% FCS, and then fixed overnight in 85% ethanol at 4° C. Before analysis, the cells are pelleted, washed once, and stained in a solution of 10 µg propidium iodide and 250 µg of ribonuclease (RNAse) A per milliliter at 37° C. for half an hour. Flow cytometry analysis is perfonned on a Becton-Dickinson FACScan, and data from 10,000 cells per sample is analyzed with Modfit software.

Monopolar Spindle Formation Following Application of a Quinazolinone KSP Inhibitor To determine the nature of G2/M accumulation, human tumor cell lines Skov-3 (ovarian), HeLa (cervical), and A549 (lung) are plated in 96-well plates at densities of 4,000 cells per well (SKOV-3 & HeLa) or 8,000 cells per well (A549), allowed to adhere for 24 hours, and treated with various concentrations of the test compounds for 24 hours. Cells are fixed in 4% formaldehyde and stained with antitubulin antibodies (subsequently recognized using fluorescently-labeled secondary antibody) and Hoechst dye (which stains DNA). The cells can be visually inspected to assess the effects of the test compounds. For example, microinjection of anti-KSP antibodies causes mitotic arrest with arrested cells displaying monopolar spindles.

Example 8

Inhibition of Cellular Proliferation in Tumor Cell Lines Treated with KSP Inhibitors Cells are plated in 96-well plates at densities from 1000-2500 cells/well (depending on the cell line) and allowed to adhere/grow for 24 hours. They are then treated with various concentrations of test compound for 48 hours. The time at which compounds are added is considered $T_o$. A tetrazolium-based assay using the reagent 3-(4,5-dimethylthiazol-2-yl)-5-(3-carboxymethoxyphenyl)-2-(4-sulfophenyl)-2H-tetrazolium (MTS) (U.S. Pat. No. 5,185,450) (see Promega product catalog #G3580, CellTiter 96®AQ$_{ueous}$ One Solution Cell Proliferation Assay) is used to determine the number of viable cells at $T_0$ and the number of cells remaining after 48 hours compound exposure. The number of cells remaining after 48 hours is compared to the number of viable cells at the time of test compound addition, allowing for calculation of growth inhibition. The growth over 48 hours of cells in control wells treated with vehicle only (0.25% DMSO) is considered 100% growth and the growth of cells in wells with compounds is compared to this. Active KSP inhibitors inhibit cell proliferation in one or more human tumor cell lines of the following tumor types: lung (NCI-H460, A549), breast (MDA-MB-231, MCF-7, MCF-7/ADR-RES), colon (HT29, HCT15), ovarian (SKOV-3, OVCAR-3), leukemia (HL-60 (TB), K-562), central nervous system (SF-268), renal (A498), osteosarcoma (U2-OS), and cervical (HeLa), and mouse tumor line (B16, melanoma).

Calculation Of $GI_{50}$: A $GI_{50}$ is calculated by plotting the concentration of compound in µM vs the percentage of cell growth of cell growth in treated wells. The $GI_{50}$ calculated for the compounds is the estimated concentration at which growth is inhibited by 50% compared to control, i.e., the concentration at which:

$$100\times[(\text{Treated}_{48}-T_0)/(\text{Control}_{48}-T_0)]=50.$$

All concentrations of compounds are tested in duplicate and controls are averaged over 12 wells. A very similar 96-well plate layout and $GI_{15}$ calculation scheme is used by the National Cancer Institute (see Monks, et al., J. Natl. Cancer Inst. 83:757-766 (1991)). However, the method by which the National Cancer Institute quantitates cell number does not use MTS, but instead employs alternative methods.

Calculation Of $IC_{50}$: Measurement of a compound's $IC_{50}$ for KSP activity uses an ATPase assay. The following solutions are used: Solution 1 consists of 3 mM phosphoenolpyruvate potassium salt (Sigma P-7127), 2 mM ATP (Sigma A-3377), 1 mM IDTT (Sigma D-9779), 5 μM paclitaxel (Sigma T-7402), 10 ppm antifoam 289 (Sigma A-8436), 25 mM Pipes/KOH pH 6.8 (Sigma P6757), 2 mM $MgCl_2$ (VWR JT400301), and 1 mM EGTA (Sigma E3889). Solution 2 consists of 1 mM NADH (Sigma N8129), 0.2 mg/ml BSA (Sigma A7906), pyruvate kinase 7U/ml, L-lactate dehydrogenase 10 U/ml (Sigma P0294), 100 nM KSP motor domain, 50 μg/ml microtubules, 1 mM DTT (Sigma D9779), 5 ;M paclitaxel (Sigma T-7402), 10 ppm antifoam 289 (Sigma A-8436), 25 mM Pipes/KOH pH 6.8 (Sigma P6757), 2 mM $MgCl_2$ (VWR JT4003-01), and 1 mM EGTA (Sigma E3889). Serial dilutions (8-12 two-fold dilutions) of the composition are made in a 96-well microtiter plate (Coming Costar 3695) using Solution 1. Following serial dilution each well has 50 μl of Solution 1. The reaction is started by adding 50 μl of Solution 2 to each well. This can be done with a multichannel pipettor either manually or with automated liquid handling devices. The microtiter plate is then transferred to a microplate absorbance reader and multiple absorbance readings at 340 nm are taken for each well in a kinetic mode. The observed rate of change, which is proportional to the ATPase rate, is then plotted as a function of the compound concentration. For a standard $IC_{50}$ determination the data acquired is fit by the following four parameter equation using a nonlinear filting program (e.g., Grafit 4):

$$y = \frac{\text{Range}}{1 + \left(\frac{x}{IC_{50}}\right)^s} + \text{Background}$$

where y is the observed rate and x the compound concentration.

Example 9

Inhibition of Cellular Viability in Tumor Cell Lines Treated with KSP Inhibitors Materials and Solutions:
Cells: SKOV3, Ovarian Cancer (human).
Media: Phenol Red Free RPMI+5% Fetal Bovine Serum+2 mM L-glutamine.
Colorimetric Agent for Determining Cell Viability: Promega MTS tetrazolium compound.
Control Compound for max cell kill: Topotecan, 1 μM.
Procedure: Day 1—Cell Plating: Adherent SKOV3 cells are washed with 10 mLs of PBS followed by the addition of 2 mLs of 0.25% trypsin and incubation for 5 minutes at 37° C. The cells are rinsed from the flask using 8 mL of media (phenol red-free RPMI+ 5% FBS) and transferred to fresh flask. Cell concentration is determined using a Coulter counter and the appropriate volume of cells to achieve 1000 cells/100 μL is calculated. 100 μL of media cell suspension (adjusted to 1000 cells/100 μL) is added to all wells of 96-well plates, followed by incubation for 18 to 24 hours at 37° C., 100% humidity, and 5% $CO_2$, allowing the cells to adhere to the plates.
Procedure: Day 2—Compound Addition: To one column of the wells of an autoclaved assay block are added an initial 2.5 μL of test compound(s) at 400× the highest desired concentration. 1.25 μL of 400×(400μM) Topotecan is added to other wells (ODs from these wells are used to subtract out for background absorbance of dead cells and vehicle). 500 μL of media without DMSO are added to the wells containing test compound, and 250 μL to the Topotecan wells. 250 μL of media +0.5% DMSO is added to all remaining wells, into which the test compound(s) are serially diluted. By row, compound-containing media is replica plated (in duplicate) from the assay block to the corresponding cell plates. The cell plates are incubated for 72 hours at 37° C., 100% humidity, and 5% $CO_2$.

Procedure: Day 4—MTS Addition and OD Reading: The plates are removed from the incubator and 40 μl MTS/PMS is added to each well. Plates are then incubated for 120 minutes at 37° C., 100% humidity, 5% $CO_2$, followed by reading the ODs at 490 nm after a 5 second shaking cycle in a ninety-six well spectrophotometer.

Data Analysis The normalized % of control (absorbance-background) is calculated and an XLfit is used to generate a dose-response curve from which the concentration of compound required to inhibit viability by 50% is determined.

The compounds of the present invention show activity when tested in one or more of the methods described in Examples 7, 8 and 9.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

We claim:

1. A compound selected from the group represented by Formula I:

Formula I where:
U—V is —N($R^6$)—$CR^eR^f$—, —$CR^eR^f$—N($R^6$)—, —N($R^6$)—$CR^eR^f$—$CR^gR^h$—, —$CR^eR^f$—N($R^6$)—$CR^g$ $R^h$— or —$CR^eR^f$—$CR^gR^h$—N($R^6$)—;

$R^a$, $R^b$, $R^c$, $R^d$, $R^e$, $R^f$, $R^g$ and $R^h$ are independently hydrogen, alkyl, aryl, aralkyl, heteroaryl, substituted alkyl, substituted aryl, substituted aralkyl or substituted heteroaryl;

$R^1$, $R^2$, $R^3$, and $R^4$ are independently hydrogen, alkyl, alkoxy, halogen, cyano or substituted alkyl;

$R^5$ is benzyl or substituted benzyl; and $R^6$ is benzyl substituted benzoyl, benzyl or subsitued benzyl;

or a pharmaceutically acceptable salt thereof.

2. The compound of claim 1, or a pharmaceutically acceptable salt thereof, where;

$R^1$, $R^2$, $R^3$ and $R^4$ are independently hydrogen, chloro, fluoro, methyl, methoxy, cyano or substituted lower alkyl;

$R^a$ to $R^h$ are independently hydrogen, lower alkyl or substituted lower alkyl;
U—V is —N($R^6$)—C$R^e R^f$—C$R^g R^h$, —C$R^e R^f$—N($R^6$)—C$R^g R^h$— or —C$R^e R^f$—C$R^g R^h$—N($R^6$)—;
$R^6$ is substituted benzyl or substituted bezoyl; and
is an (R)-enantiomer.

3. The compound of claim 2, or a pharmaceutical acceptable salt thereof, where:
$R^1$, $R^2$, $R^3$ and $R^4$ are independently hydrogen, chloro, fluoro, methyl, methoxy or cyano;
no more than one of $R^a$ to $R^h$ is other than hydrogen;
U—V is —N($R^6$)—C$R^e R^f$—C$R^g R^h$— or —C$R^e R^f$—N($R^6$)—C$R^g R^h$—; and
$R^6$ is optionally substituted benzoyl.

4. A compound selected from the group represented by Formula I:

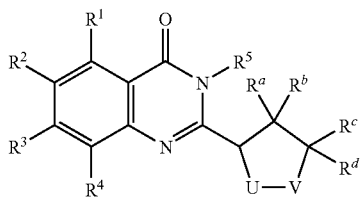

Formula I where:
$R^1$, $R^2$, $R^3$ and $R^4$ are hydrogen, or three of $R^1$, $R^2$, $R^3$ and $R^4$ are hydrogen and the fourth is halo, methoxy, methyl or cyano;
$R^5$ is benzyl;
$R^a$ to $R^h$ are hydrogen;
U—V is —N($R^6$)—C$R^e R^f$—C$R^g R^h$—; and
$R^6$ is p-methyl-benzoyl;
or a pharmaceutically acceptable salt thereof.

5. The compound of claim 4, or a pharmaceutically acceptable salt thereof where: $R^1$, $R^2$ and $R^4$ are hydrogen and $R^3$ is hydrogen or chloro.

6. The compound of claim 1, selected from:
3-benzyl-7-chloro-2-[1-(4-methyl-benzyl)-pyrrolidin-2-yl]-3H-quinazolin-4-one;
3-benzyl-7-chloro-2-[1-(4-methyl-benzoyl)-pyrrolidin-2-yl]-3H-quinazolin-4-one;
3-beznyl-7-chloro-2-[1-(4-methyl-benzoyl)-piperidin-2-yl]-3H-quinazolin-4-one;
3-beznyl-7-chloro-2-[1-(4-methyl-benzoyl)-piperidin-3-yl]-3H-quinazolin-4-one;
3-beznyl-7-chloro-2-[1-(4-methyl-benzoyl)-piperidin-3-yl]-3H-quinazolin-4-one;
3-benzyl-7-chloro-2-[1-(4-methyl-benzoyl)-piperidin-4-yl]-3H-quinazolin-4-one; and
3-benzyl-7-chloro-2-[1-(4-methyl-benzoyl)-piperidin-4-yl]-3H-quinazolin-4-one;or a pharmaceutically acceptable salt thereof.

7. The compound of claim 6, or a pharmaceutically acceptable salt thereof, that is an (R)-enantiomer.

8. The compound of claim 1, selected from:
3-benzyl-7-chloro-2-[1-(4-methyl-benzoyl)-pyrrolidin-2-yl]-3H-quinazolin-4-one;
3-benzyl-7-chloro-2-[1-(4-methyl-benzoyl )-piperidin-2-yl]-3H-quinazolin-4-one;
3-benzyl-7-chloro-2-[1-(4-methyl-benzoyl)-piperidin-3-yl]-3H-quinazolin-4-one; and
3-benzyl-7-chloro-2-[1-(4-methyl-benzoyl)-piperidin-4-yl]-3H-quinazolin-4-one; or a pharmaceutically acceptable salt thereof.

9. The compound of claim 8, or a pharmaceutically acceptable salt thereof, that is an (R)-enantiomer.

10. The compound of claim 1, selected from:
3-benzyl-7-chloro-2-[1-(4-methyl-benzoyl)-piperid in-2-yl]-3H-quinazolin-4-one; and
3-benzyl-7-chloro-2-[1-(4-methyl-benzoyl)-piperid in-3-yl]-3H-quinazolin-4-one; or a pharmaceutically acceptable salt thereof.

11. The compound of claim 10, or a pharmaceutically acceptable salt thereof, that is an (R)-enantiomer.

12. A pharmaceutical formulation comprising a pharmaceutical acceptable excipient and an effective amount of a compound of claim 1, or a pharmaceutically acceptable salt thereof.

13. The compound of claim 1, or a pharmaceutically acceptable salt thereof, where U—V is —N($R^6$)—C$R^e R^f$—C$R^g R^h$, —C$R^e R^f$—N($R^6$)—C$R^g R^h$ or —C$R^e R^f$—C$R^g R^h$—N($R^6$)—.

14. The compound of claim 13, or a pharmaceutically acceptable salt thereof, where U—V is —N($R^6$)—C$R^e R^f$—C$R^g R^h$— or —C$R^e R^f$—N($R^6$)—C$R^g R^6$—.

15. The compound of claim 14, or a pharmaceutically acceptable salt thereof, where U—V is —N($R^6$)—C$R^e R^f$—C$R^g R^h$—.

16. The compound of claim 15, or a pharmaceutically acceptable salt thereof, where U—V is —N($R^6$)—CH$_2$—CH$_2$—.

17. The compound of claim 1, or a pharmaceutically acceptable salt thereof, where $R^1$, $R^2$, $R^3$ and $R^4$ are independently hydrogen, chioro, fluoro, methyl, methoxy, cyano or substituted lower alkyl.

18. The compound of claim 17, or a pharmaceutically acceptable salt thereof, where $R^1$, $R^2$, $R^3$ and $R^4$ are independently hydrogen, chloro, fluoro, methyl,. methoxy or cyano.

19. The compound of claim 18, or a pharmaceutically acceptable salt thereof, where $R^1$, $R^2$, $R^3$ and $R^4$ are hydrogen.

20. The compound of claim 18, or a pharmaceutically acceptable salt thereof, where three of $R^1$, $R^2$, $R^3$ and $R^4$ are hydrogen and the fourth is halo, methoxy, methyl or cyano.

21. The compound of claim 18, or a pharmaceutically acceptable salt thereof, where $R^1$, $R^2$ and $R^4$ are hydrogen and $R^3$ is hydrogen or chloro.

22. The compound of claim 1, or a pharmaceutically acceptable salt thereof, where $R^5$ is benzyl.

23. The compound of claim 1, or a pharmaceutically acceptable salt thereof, where $R^a$ to $R^h$ are independently hydrogen, lower alkyl or substituted lower alkyl.

24. The compound of claim 23, or a pharmaceutically acceptable salt thereof, where $R^a$ to $R^h$ are hydrogen.

25. The compound of claim 1, or a pharmaceutically acceptable salt thereof, where $R^6$ is substituted benzyl or substituted benzoyl.

26. The compound of claim 25, or a pharmaceutically acceptable salt thereof, where $R^6$ is optionally substituted benzoyl.

27. The compound of claim 26, or a pharmaceutically acceptable salt thereof, where $R^6$ is p-methyl-benzoyl.

28. The compound of claim 1, or a pharmaceutically acceptable salt thereof, wherein the compound is an (R)-enantiomer.

* * * * *

UNITED STATES PATENT AND TRADEMARK OFFICE
CERTIFICATE OF CORRECTION

PATENT NO. : 7,557,115 B2 Page 1 of 1
APPLICATION NO. : 10/529745
DATED : July 7, 2009
INVENTOR(S) : Bergnes et al.

It is certified that error appears in the above-identified patent and that said Letters Patent is hereby corrected as shown below:

On the Title page,

[*] Notice:   Subject to any disclaimer, the term of this patent is extended or adjusted under 35 USC 154(b) by (406) days Delete the phrase "by 406 days" and insert -- by 460 days --

Signed and Sealed this

Nineteenth Day of January, 2010

David J. Kappos
*Director of the United States Patent and Trademark Office*

UNITED STATES PATENT AND TRADEMARK OFFICE
CERTIFICATE OF CORRECTION

PATENT NO.       : 7,557,115 B2
APPLICATION NO. : 10/529745
DATED            : July 7, 2009
INVENTOR(S)      : Bergnes et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 924 days.

Signed and Sealed this

Seventh Day of September, 2010

David J. Kappos
*Director of the United States Patent and Trademark Office*